US010981995B2

(12) United States Patent
Zheng et al.

(10) Patent No.: US 10,981,995 B2
(45) Date of Patent: Apr. 20, 2021

(54) ANTI-PD-L1 ANTIBODIES

(71) Applicants: WUXI BIOLOGICS (SHANGHAI) CO. LTD., Shanghai (CN); Wuxi Biologics Ireland Limited, Dublin (IE)

(72) Inventors: Yong Zheng, Shanghai (CN); Jing Li, Lexington, MA (US); Zhisheng Chen, Shanghai (CN)

(73) Assignees: Wuxi Biologies Ireland Limited, Dublin (IE); Wuxi Biologies (Shanghai) Co. Ltd., Shanghai (CN)

(*) Notice: Subject to any disclaimer, the term of this patent is extended or adjusted under 35 U.S.C. 154(b) by 428 days.

(21) Appl. No.: 15/749,783

(22) PCT Filed: Aug. 5, 2016

(86) PCT No.: PCT/CN2016/093560
§ 371 (c)(1),
(2) Date: Feb. 2, 2018

(87) PCT Pub. No.: WO2017/020858
PCT Pub. Date: Feb. 9, 2017

(65) Prior Publication Data
US 2020/0140554 A1    May 7, 2020

(30) Foreign Application Priority Data

Aug. 6, 2015   (WO) .............. PCT/CN2015/086216

(51) Int. Cl.
| C07K 16/28 | (2006.01) |
| G01N 33/68 | (2006.01) |
| A61P 35/00 | (2006.01) |
| A61K 39/00 | (2006.01) |

(52) U.S. Cl.
CPC ..... *C07K 16/2827* (2013.01); *G01N 33/6893* (2013.01); *A61K 2039/505* (2013.01); *A61P 35/00* (2018.01); *C07K 2317/21* (2013.01); *C07K 2317/565* (2013.01); *C07K 2317/76* (2013.01); *C07K 2317/92* (2013.01); *G01N 2800/52* (2013.01)

(58) Field of Classification Search
None
See application file for complete search history.

(56) References Cited

U.S. PATENT DOCUMENTS

| 30,985 | A | 12/1860 | Pye |
| 4,560,655 | A | 12/1985 | Baker |
| 4,657,866 | A | 4/1987 | Kumar |
| 4,767,704 | A | 8/1988 | Cleveland et al. |
| 4,927,762 | A | 5/1990 | Darfler |
| 5,122,469 | A | 6/1992 | Mather et al. |
| 6,005,079 | A | 12/1999 | Casterman et al. |
| 7,943,743 | B2 | 5/2011 | Korman et al. |
| 8,779,108 | B2 | 7/2014 | Queva et al. |
| 8,907,157 | B2 | 12/2014 | Buelow |
| 9,624,298 | B2 * | 4/2017 | Nastri ................ A61P 1/00 |
| 9,676,863 | B2 * | 6/2017 | Lo .................... A61P 1/18 |
| 9,856,308 | B2 * | 1/2018 | Hedhammar .......... C07K 16/44 |
| 2014/0099254 | A1 | 4/2014 | Chang et al. |
| 2014/0219956 | A1 | 8/2014 | Govindan et al. |
| 2014/0341917 | A1 | 11/2014 | Nastri et al. |

FOREIGN PATENT DOCUMENTS

| CN | 101104540 A | 1/2008 |
| CN | 101104640 A | 1/2008 |
| CN | 101663323 A | 3/2010 |
| CN | 102264762 A | 11/2011 |
| EA | 019344 B1 | 3/2014 |
| EP | 0404097 | 12/1990 |
| EP | 2152880 | 8/2011 |
| EP | 2336329 | 10/2012 |
| JP | 2013511959 A | 4/2013 |
| JP | 2015500207 A | 1/2015 |
| RU | 2011128399 A | 1/2013 |
| WO | 8700195 | 1/1987 |
| WO | 9003430 | 4/1990 |
| WO | 99311161 | 6/1993 |
| WO | 94/04678 | 3/1994 |
| WO | 94/25591 | 11/1994 |
| WO | 2007005874 | 1/2007 |
| WO | 2007005874 A2 | 1/2007 |
| WO | 2010077634 | 7/2010 |
| WO | 2010077634 A1 | 7/2010 |
| WO | 2011066389 | 6/2011 |
| WO | 2013181634 A2 | 12/2013 |
| WO | 2013181635 | 12/2013 |
| WO | 2014055897 | 4/2014 |

(Continued)

OTHER PUBLICATIONS

Mariuzza, R.A. etal. The Structural Basis of Antigen-Antibody Recognition1 Annu. Rev. Biophys. Biphys. Chem. 16:139-159, 1987.*
Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*

(Continued)

*Primary Examiner* — Nora M Rooney
(74) *Attorney, Agent, or Firm* — Goodwin Procter LLP

(57) ABSTRACT

The present disclosure provides monoclonal antibodies against protein programmed cell death 1 ligand (PD-L1), which can block the binding of PD-L1 to PD-1, and therefore block the inhibitory function of PD-L1 on PD-1 expressing T cells. The antibodies of disclosure provide very potent agents for the treatment of multiple cancers via modulating human immune function.

17 Claims, 10 Drawing Sheets

Specification includes a Sequence Listing.

(56) References Cited

FOREIGN PATENT DOCUMENTS

| WO | 2014055897 A2 | 4/2014 |
|---|---|---|
| WO | 2014100079 | 6/2014 |
| WO | 2014100079 A1 | 6/2014 |
| WO | 2015/036499 | 3/2015 |
| WO | 2015085847 | 6/2015 |
| WO | 2016/023875 | 2/2016 |

OTHER PUBLICATIONS

Poosarla et al. 'Computational De Novo Design of Antibodies Binding to a Peptide With High Affinity.' Biotech. Bioeng. 114(6): 1331-1342, 2017.*
Diamond, B. et al., "Somatic mutation of the T15 heavy chain gives rise to an antibody with autoantibody specificity", Proceedings of the National Academy of Sciences (Sep. 1984), vol. 81, pp. 5841-5844, the abstract.
Jarilin A.A., "Osnovy immunologii", M.: Medicina, 1999, pp. 172-174.
Kang, A. S. et al., "Antibody redesign by chain shuffling from random combinatorial immunoglobulin libraries", Proceedings of the National Academy of Sciences (Dec. 1991), vol. 88(24), pp. 11120-11123, see p. 11122, Table 4.
Ohno, S. et al., "Antigen-binding specificities of antibodies are primarily determined by seven residues of VH", Proceedings of the National Academy of Sciences (May 1985), vol. 82, pp. 2945-2949, the abstract.
Ozhegov S.I., 'Shvedova N.Yu. Tolkovyj slovar' russkogo yazyka: 80 000 slov i frazeologicheskich vyrajenii, ed 4, suppl, M.: LLC "A Temp", 2006, 944 pages, p. 375.
Rudikoff S. et al., "Single amino acid substitution of altering antigen-binding specificity", Proc. Nat. Acad. Sci. USA. Immunology (Mar. 1982), vol. 79, pp. 1979-1983: abstract on p. 1979.
Al-Lazikani, B., Chothia, C., Lesk, A. M., Standard Conformations for the Canonical Structures of Immunoglobulins, J. Mol. Biol., 273(4), 927-948 (1997).
Chothia, C. et al., Domain Association in Immunoglobulin Molecules, J. Mol. Biol., Dec. 5;186(3):651-63 (1985).
Chothia, C. and Lesk, A.M., Canonical Structures for the Hypervariable Regions of Immunoglobulins, J. Mol. Biol., 196,901-917 (1987).
Chothia, C. et al., Conformations of Immunoglobulin Hypervariable Regions, Nature, Dec. 21-28;342(6252):877-83 (1989).
Kabat E.A. et al., National Institutes of Health, Bethesda, Md. (1991).
Riechmann L. and Muyldermans S., Single domain antibodies: comparison of camel VH and camelised human VH domains, J Immunol Methods. Dec. 10;231(1-2):25-38 (1999).
Muyldermans S., Single domain camel antibodies: current status, Rev Mol Biotechnol. Jun.;74(4):277-302 (2001).
Hamers-Casterman C. et al., Naturally occurring antibodies devoid of light chains, Nature. Jun. 3;363(6428):446-8 (1993).
Nguyen VK. et al. "Heavy-chain antibodies in Camelidae; a case of evolutionary innovation," Immunogenetics. Apr.;54(1):39-47 (2002).
Nguyen VK. et al., Heavy-chain only antibodies derived from dromedary are secreted and displayed by mouse B cells, Immunology. May;109(1):93-101 (2003).
Koch-Nolte F. et al., Single domain antibodies from llama effectively and specifically block T cell ecto-ADP-ribosyltransferase ART2.2 in vivo, Faseb J. Nov.;21(13):3490-8. Epub Jun. 15, 2007 (2007).
Holliger P. et al., "Diabodies": Small bivalent and bispecific antibody fragments, Proc Natl Acad Sci U S A. Jul. 15;90 (14):6444-8 (1993).
Gordon J. Freeman et al., Engagement of the PD-1 immunoinhibitory receptor by a novel B7 family member leads to negative regulation of lymphocyte activation, vol. 192, No. 7, Oct. 2, 2000 1027-1034.
Altschul S.F. et al, Basic Local Alignment Search Tool, J. Mol. Biol., 215:403-410 (1990).
Stephen F. et al, Gapped BLAST and PSI-BLAST: a new generation of protein database search programs, Nucleic Acids Res., 25:3389-3402 (1997).
Higgins D.G. et al, Using CLUSTAL for Multiple Sequence Alignments, Methods in Enzymology, 266:383-402 (1996).
Larkin M.A. et al, Clustal W and Clustal X version 2.0, Bioinfomiatics (Oxford, England), 23(21): 2947-8 (2007).
Graham et al., Characteristics of a Human Cell Line Transformed by DNA from Human Adenovirus Type 5, J. Gen Virol. 36:59 (1977).
Urlaub et al., Isolation of Chinese Hamster Cell Mutants Deficient in Dihydrofolate Reductase Activity, Proc. Natl. Acad. Sci. USA 77:4216 (1980).
J. P. Mather, Establishment and Characterization of Two Distinct Mouse Testicular Epithelial Cell Lines, Biol. Reprod. 23:243-251 (1980).
Mather et al., Culture of testicular cells in hormone-supplemented serum-free medium, Annals N.Y. Acad. Sci. 383:44-68 (1982).
Barnes et al., Methods for Growth of Cultured Cells in Serum-Free Medium, Anal. Biochem. 102:255 (1980).
Carter et al., High Level *Escherichia coli* Expression and Production of a Bivalent Humanized Antibody Fragment, Bio/Technology 10:163-167 (1992).
Lindmark et al., Binding of Immunoglobulins to Protein A and Immunoglobulin Levels in Mammalian Sera, J. Immunol. Meth. 62:1-13 (1983).
Guss et al., Structure of the IgG-binding regions of streptococcal protein G, EMBO J. 5:1567-1575 (1986).
International Search Report of PCT application No. PCT/CN2016/093560 dated Aug. 5, 2016.
Michael J. Osborn et al., High-Affinity IgG Antibodies Develop Naturally in Ig-Knockout Rats Carrying Germline Human IgH/Igκ/Igλ Loci Bearing the Rat CH Region, The Journal of Immunology, 2013, 190: 1481-1490.
Ma B. et al, Human antibody expression in transgenic rats: Comparison of chimeric IgH loci with human VH, D and JH but bearing different rat C-gene regions, Journal of Immunological Methods 400-401 (2013) 78-86.
Geurts A. et al, Knockout Rats Produced Using Designed Zinc Finger Nucleases, Science. Jul. 24, 2009; 325(5939): 433. doi:10.1126/science.1172447.
Lonberg, N. et al., Antigen-specific human antibodies from mice comprising four distinct genetic modifications, Nature 368(6474): 856-859 (1994).
Mendez et al., Functional transplant of megabase human immunoglobulin loci recapitulates human antibody response in mice, Nat Genet., 1997, 15:146-156.
Ishida et al., Production of human monoclonal and polyclonal antibodies in TransChromo animals, Cloning Stem Cells, 2002,4:91-102.
Murphy et al., Mice with megabase humanization of their immunoglobulin genes generate antibodies as efficiently as normal mice, Proc Natl Acad Sci USA, 2014, 111:5153-5158.
Lee et al., Complete humanization of the mouse immunoglobulin loci enables efficient therapeutic antibody discovery, Nat Biotechnol, 2014, 32:356-363.
Flisikowska et al., Efficient immunoglobulin gene disruption and targeted replacement in rabbit using zinc finger nucleases, PLoS One, 2011, 6:e21045.
International Search Report of PCT application No. PCT/CN2015/086216 dated Aug. 6, 2015.
Cristina Teixido Niki Karachaliou Maria Gonzalez-Cao Daniela Morales-Espinosa Rafael Rosell: "Assays for predicting and monitoring responses to lung cancer immunotherapy", Jan. 1, 2015, pp. 87-95, XP55528318, China, Retrieved from the Internet: URL: https://www.ncbi.nlm.nih.gov/pmc/articles/PMC4493376/pdf/cbm-12-02-087.pdf.
Kathleen M. Mahoney et al: "The Next Immune-Checkpoint Inhibitors: PD-1/PD-L1 Blockade in Melanoma", Clinical Therapeutics., vol. 37, No. 4, Apr. 1, 2015, pp. 764-782, XP055285031, US.
The extended European search report in EP application No. 16832346.7, dated Dec. 11, 2018.

(56) References Cited

OTHER PUBLICATIONS

Antje Habicht et al., A Link between PDL1 and T Regulatory Cells in Fetomaternal Tolerance, J Immunol 2007; 179:5211-5219, doi: 10.4049/jimmunol.179.8.5211.

Jun Konishi et al., B7-H1 Expression on Non-Small Cell Lung Cancer Cells and its Relationship with Tumor-Infiltrating Lymphocytes and Their PD-1 Expression, Clinical Cancer Research, vol. 10, 5094-5100, Aug. 1, 2004.

Haidong Dong and Lieping Chen, B7-H1 pathway and its role in the evasion of tumor immunity, J Mol Med (2003) 81:281-287 DOI 10.1007/s00109-003-0430-2.

Gordon J. Freeman et al., Engagement of the PD-1 Immunoinhibitory Receptor by a Novel B7 Family Member Leads to Negative Regulation of Lymphocyte Activation, J. Exp. Med., vol. 192, No. 7, Oct. 2, 2000, 1027-1034.

Yan Luan et al., A fully human monoclonal antibody targeting PD-L1 with potent anti-tumor activity, International Immunopharmacology 31 (2016) 248-256.

Christian Blank et al., Interaction of PD-L1 on tumor cells with PD-1 on tumor-specific T cells as a mechanism of immune evasion: implications for tumor immunotherapy, Cancer Immunol Immunother (2005) 54: 307-314, DOI 10.1007/s00262-004-0593-x.

Taku Okazaki and Tasuku Honjo., PD-1 and PD-1 ligands: from discovery to clinical application, International Immunology, vol. 19, No. 7, pp. 813-824, doi:10.1093/intimm/dxm057.

Manish J. Butte et al., PD-L1 interacts specifically with B7-1 to inhibit T cell proliferation, Immunity. Jul. 2007 ; 27(1): 111-122. doi:10.1016/j.immuni.2007.05.016.

Yvette Latchman et al., PD-L2 is a second ligand for PD-1 and inhibits T cell activation, Nature Immunology, vol. 2, No. 3, · Mar. 2001, DOI: 10.1038/85330.

Loise M. Francisco et al., The PD-1 Pathway in Tolerance and Autoimmunity, Immunol Rev. Jul. 2010 ; 236: 219-242. doi:10. 1111/j.1600-065X.2010.00923.x.

AbYsis Accession: CAF32932.1; abYsis-EMBL-IG: CBJ04748.1, Published on Mar. 3, 2004.

AbYsis Accession: AAC26479.1; abYsis-EMBL-IG U93176, Published on Mar. 2, 1998.

AbYsis Accession: 044060; abYsis-EMBL-044060, Published on Apr. 28, 1999.

AbYsis Accession: CAB51317.1; abYsis-EMBL-IG AJ388666, Published on Jul. 22, 1999.

Julie B. Brahmer et al.,"Safety and Activity of Anti-PD-L1 Antibody in Patients with Advanced Cancer", The New England Journal of Medicine (2012), vol. 366, pp. 2455-2465.

The First Office Action with search report for Chinese Patent Application No. 201610638134.5, dated Nov. 13, 2020.

\* cited by examiner

| Sample | KD | | |
|---|---|---|---|
| | Best fit-Bmax | Best fit-KD | Std. Error-KD |
| 1.14.4 | 7.37E-12 | 3.92E-10 | 3.27E-11 |
| 1.4.1 | 7.06E-12 | 4.78E-10 | 2.37E-11 |
| 1.46.11 | 7.11E-12 | 3.76E-10 | 4.13E-11 |
| 1.20.15 | 7.21E-12 | 2.26E-10 | 2.13E-11 |

1.14.4

ANTI-PD-L1 ANTIBODIES

FIELD OF THE INVENTION

The present disclosure generally relates to novel anti-PD-L1 antibodies.

BACKGROUND

Increasing evidences from preclinical and clinical results have shown that targeting immune checkpoints is becoming the most promising approach to treat patients with cancers. Programmed cell death 1, one of immune-checkpoint proteins, play a major role in limiting the activity of T cells that provide a major immune resistance mechanism by which tumor cells escaped immune surveillance. The interaction of PD-1 expressed on activated T cells, and PD-L1 expressed on tumor cells negatively regulate immune response and damp anti-tumor immunity. Expression of PD-L1 on tumors is correlated with reduced survival in esophageal, pancreatic and other types of cancers, highlighting this pathway as a new promising target for tumor immunotherapy. Multiple agents targeting PD-1 pathway have been developed by pharmaceutical companies, such as Bristol-Myers Squibb (BMS), Merck, Roche and GlaxoSmithKline (GSK). Data from clinical trials demonstrated early evidence of durable clinical activity and an encouraging safety profile in patients with various tumor types. Nivolumab, a PD-1 drug developed by BMS, is being put at center stage of the next-generation field. Now in 6 late-stage studies, the treatment spurred tumor shrinkage in three of 5 cancer groups studied, including 18% of 72 lung cancer patients, close to a third of 98 melanoma patients and 27% of 33 patients with kidney cancer. Developed by Merck, lambrolizumab is a fully human monoclonal IgG4 antibody that acts against PD-1, which grabbed the FDA's new breakthrough designation after impressive IB data came through for skin cancer. The results from a phase IB study have shown an objective anti-tumor response in 51% of 85 cancer patients, and a complete response in 9% of patients. Roche's experimental MPDL3280A demonstrated an ability to shrink tumors in 29 of 140 (21%) advanced cancer patients with various tumor sizes.

However, the existing therapies may not be all satisfactory and therefore new anti-PD-L1 antibodies are still needed.

BRIEF SUMMARY OF THE INVENTION

The present disclosure provides novel monoclonal anti-PD-L1 antibodies (in particular fully human antibodies), polynucleotides encoding the same, and methods of using the same.

In one aspect, the present disclosure provides isolated monoclonal antibodies or antigen binding fragments thereof, which are capable of specifically binding to human PD-L1 at a Kd value no more than $10^{-9}$ M (e.g. no more than $\leq 9 \times 10^{-10}$ M, $\leq 8 \times 10^{-10}$ M, $\leq 7 \times 10^{-10}$ M, $\leq 6 \times 10^{-10}$ M, $\leq 5 \times 10^{-10}$ M, $\leq 4 \times 10^{-10}$ M, $\leq 3 \times 10^{-10}$ M, $\leq 2 \times 10^{-10}$ M, or $\leq 10^{-10}$ M) as measured by plasmon resonance binding assay.

In certain embodiments, the antibodies or antigen binding fragments thereof bind to monkey PD-L1 at an EC50 of no more than 10 nM (e.g. no more than 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM. In certain embodiments, the antibodies and antigen-binding fragments thereof do not bind to mouse PD-L1 but bind to monkey PD-L1 with a binding affinity similar to that of human PD-L1. In certain embodiments, the antibodies or antigen binding fragments thereof potently inhibit binding of human or monkey PD-L1 to its receptor (e.g. PD-1), at an IC50 of no more than 100 nM (e.g. no more than 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM). In certain embodiments, the EC50 or IC50 is measured by fluorescence-activated cell sorting (FACS) analysis.

In certain embodiments, the antibodies or antigen binding fragments thereof have substantially reduced effector function. In certain embodiments, the antibodies or antigen binding fragments thereof do not mediate ADCC or CDC or both.

In certain embodiments, the antibodies or antigen binding fragments thereof provided herein comprise a heavy chain CDR sequences selected from the group consisting of: SEQ ID NOs: 1, 3, 5, 13, 15, 17, 25, 27, 29, 37, 39 and 41.

In one aspect, the antibodies or an antigen binding fragments thereof provided herein comprise a light chain CDR sequences selected from the group consisting of: SEQ ID NOs: 7, 9, 11, 19, 21, 23, 31, 33 and 35.

In certain embodiments, the antibodies or antigen binding fragments thereof provided herein comprise at least one, two, three, four, five or six CDRs selected from the group consisting of: SEQ ID NOs: 1, 3, 5, 7, 9, and 11; or selected from the group consisting of: SEQ ID NOs: 13, 15, 17, 19, 21 and 23; or selected from the group consisting of: SEQ ID NOs: 25, 27, 29, 31, 33 and 35; or selected from the group consisting of: SEQ ID NOs: 37, 39, 41, 19, 21, and 23.

In certain embodiments, the antibodies or antigen binding fragments thereof provided herein comprise a heavy chain variable region selected from the group consisting of:
  a) a heavy chain variable region comprising SEQ ID NO: 1, SEQ ID NO: 3, and/or SEQ ID NO: 5;
  b) a heavy chain variable region comprising SEQ ID NO: 13, SEQ ID NO: 15, and/or SEQ ID NO: 17;
  c) a heavy chain variable region comprising SEQ ID NO: 25, SEQ ID NO: 27, and/or SEQ ID NO: 29; and
  d) a heavy chain variable region comprising SEQ ID NO: 37, SEQ ID NO: 39, and/or SEQ ID NO: 41.

In certain embodiments, the antibodies or antigen binding fragments thereof provided herein comprise a light chain variable region selected from the group consisting of:
  a) a light chain variable region comprising SEQ ID NO: 7, SEQ ID NO: 9, and/or SEQ ID NO: 11;
  b) a light chain variable region comprising SEQ ID NO: 19, SEQ ID NO: 21, and/or SEQ ID NO: 23; and
  c) a light chain variable region comprising SEQ ID NO: 31, SEQ ID NO: 33, and/or SEQ ID NO: 35.

In certain embodiments, the antibodies or antigen binding fragments thereof provided herein comprise:
  a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11;
  b) a heavy chain variable region comprising SEQ ID NO: 13, SEQ ID NO: 15, and/or SEQ ID NO: 17; and a light chain variable region comprising SEQ ID NO: 19, SEQ ID NO: 21, and/or SEQ ID NO: 23;
  c) a heavy chain variable region comprising SEQ ID NO: 25, SEQ ID NO: 27, and/or SEQ ID NO: 29; and a light chain variable region comprising SEQ ID NO: 31, SEQ ID NO: 33, and/or SEQ ID NO: 35; or d) a heavy chain variable region comprising SEQ ID NO: 37, SEQ ID NO: 39, and/or SEQ ID NO: 41 and a light chain variable region comprising SEQ ID NO: 19, SEQ ID NO: 21, and/or SEQ ID NO: 23.

In certain embodiments, the antibodies or antigen binding fragments thereof provided herein comprise a heavy chain variable region selected from the group consisting of: SEQ ID NO: 43, SEQ ID NO: 47, SEQ ID NO: 51 and SEQ ID NO: 55.

In certain embodiments, the antibodies or antigen binding fragments provided herein comprise a light chain variable region selected from the group consisting of: SEQ ID NO: 45, SEQ ID NO: 49 and SEQ ID NO: 53.

In certain embodiments, the antibodies or antigen binding fragments thereof provided herein comprise:
 a) a heavy chain variable region comprising SEQ ID NO: 43; and a light chain variable region comprising SEQ ID NO: 45;
 b) a heavy chain variable region comprising SEQ ID NO: 47; and a light chain variable region comprising SEQ ID NO: 49;
 c) a heavy chain variable region comprising SEQ ID NO: 51; and a light chain variable region comprising SEQ ID NO: 53; or
 d) a heavy chain variable region comprising SEQ ID NO: 55; and a light chain variable region comprising SEQ ID NO: 49.

In certain embodiments, the antibodies provided herein include, for example, 1.4.1, 1.14.4, 1.20.15, and 1.46.11.

In certain embodiments, the antibodies or antigen binding fragments thereof provided herein compete for the same epitope with antibodies 1.4.1, 1.14.4, 1.20.15, and 1.46.11. In certain embodiments, the antibodies or antigen binding fragments thereof provided herein bind to the epitope comprising at least one of the following amino acid residues of PD-L1: E58, E60, D61, K62, N63 and R113.

In certain embodiments, the antibodies or antigen binding fragments thereof are capable of blocking binding of human PD-L1 to its receptor and thereby providing at least one of the following activities:
 a) inducing production of IL-2 in CD4+T cells;
 b) inducing production of IFNγ in CD4+T cells;
 c) inducing proliferation of CD4+T cells and
 d) reversing T reg's suppressive function.

In certain embodiments, the antibodies provided herein are a monoclonal antibody, fully human antibody, humanized antibody, chimeric antibody, recombinant antibody, bispecific antibody, labeled antibody, bivalent antibody, or anti-idiotypic antibody.

In certain embodiments, the antigen-binding fragments thereof provided herein are a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In certain embodiments, the antibodies or antigen-binding fragments thereof provided herein further comprise an immunoglobulin constant region.

In certain embodiments, the antibodies or antigen-binding fragments thereof provided herein, further comprise a conjugate.

In certain embodiments, the conjugate can be a detectable label, a pharmacokinetic modifying moiety, or a purification moiety.

In another aspect, the present disclosure provides isolated polynucleotides encoding the antibodies or antigen binding fragments thereof provided herein. In certain embodiments, polynucleotides are provided that encode the amino acid sequences of the antibodies or antigen-binding fragments disclosed herein. In certain other embodiments, vectors are provided that comprise these polynucleotides, and in certain other embodiments, host cells are provided that comprise these vectors. In certain embodiments, methods are provided for expressing one or more of the antibodies or antigen-binding fragments disclosed herein by culturing these host cells under conditions in which the antibodies or antigen-binding fragments encoded by the polynucleotides are expressed from a vector. In certain embodiments, the polynucleotides provided herein are operably associated with a promoter such as a SV40 promoter in a vector. In certain embodiments, host cells comprising the vectors provided herein are Chinese hamster ovary cell, or 293F cell.

In another aspect, the present disclosure provides kits comprising the antibody or antigen-binding fragment thereof.

In another aspect, the PD-L1 antibodies provided herein, such as the 1.4.1, 1.14.4, 1.20.15 and 1.46.11 have good tolerability and high in vivo anti-tumor activity in an animal. In certain embodiments, an animal having tumor cells administered with the PD-L1 antibodies provided herein has a reduction of the tumor volume by at least 20%, at least 30%, at least 40%, at least 50%, at least 60%, at least 70%, at least 80%, at least 90% or at least 95% as compared to the control animal having similar baseline tumor volume but administered only with vehicle.

In another aspect, the present disclosure provides methods of detecting presence or level of PD-L1 (e.g. human or monkey) in a biological sample, comprising exposing the biological sample to the antibody or antigen-binding fragment thereof provided herein, and determining the presence or level of the PD-L1 in the sample.

In another aspect, the present disclosure provides methods of identifying an individual having a disorder or condition likely to respond to a PD-L1 antagonist, comprising: determining presence or level of PD-L1 (e.g. human or monkey) in a test biological sample from the individual with the antibody or antigen-binding fragment thereof provided herein, wherein presence or upregulated level of the PD-L1 in the test biological sample indicates likelihood of responsiveness. In certain embodiments, the methods further comprise administering an effective amount of the antibody or antigen-binding fragment thereof provided herein to the individual who has been identified as having a disorder or condition likely to respond to a PD-L1 antagonist.

The present disclosure further provides methods of monitoring therapeutic response or disease progression in a subject treated with a PD-L1 antagonist, comprising determining presence or level of PD-L1 (e.g. human or monkey) in a test biological sample from the individual with the anti-PD-L1 antibody or antigen-binding fragment thereof provided herein.

In another aspect, the present disclosure provides pharmaceutical compositions comprising the antibody or antigen-binding fragment thereof provided herein and one or more pharmaceutically acceptable carriers. In certain of these embodiments, the pharmaceutical carriers may be, for example, diluents, antioxidants, adjuvants, excipients, or non-toxic auxiliary substances.

In another aspect, the present disclosure provides methods of treating a condition in a subject that would benefit from upregulation of immune response, comprising administering an effective amount of the antibody or antigen-binding fragment thereof provided herein to the subject. In certain embodiments, the subject has upregulated expression of PD-L1.

Use of the antibody or antigen-binding fragment thereof provided herein in the manufacture of a medicament for treating a condition that would benefit from upregulation of immune response. In certain embodiments, the condition is cancer or chronic viral infection.

DETAILED DESCRIPTION OF THE INVENTION

Figure 1:
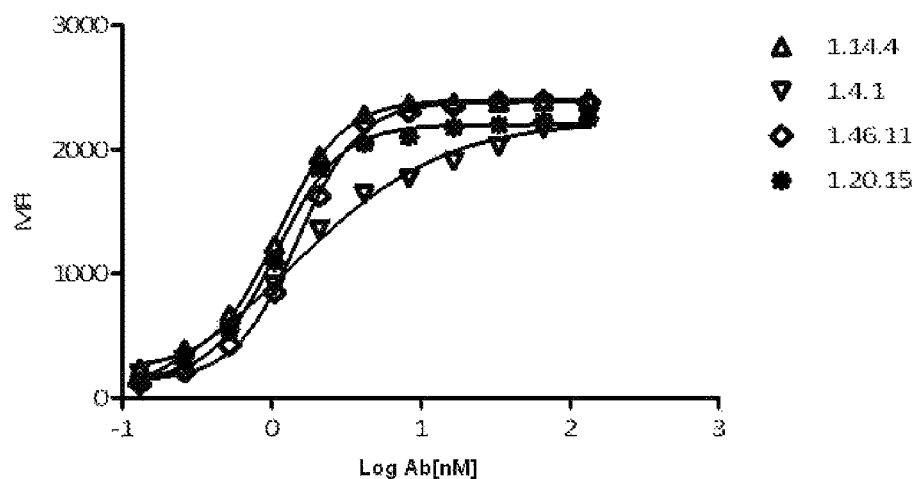
FIG. 1 presents the binding of fully human PD-L1 antibodies to PD-1 expressing CHO cell as measured by FACS analysis.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

DEFINITIONS

The term "antibody" as used herein includes any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody. An antigen-binding fragment is capable of binding to the same antigen to which the parent antibody binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')2" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879 (1988)).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363(6428):446-8 (1993); Nguyen V K. et al. "Heavy-chain antibodies in Camelidae; a case of evolutionary innovation," Immunogenetics. April; 54(1):39-47 (2002); Nguyen V K. et al. Immunology. May; 109(1): 93-101 (2003)). The variable domain of a heavy chain antibody (VHH domain) represents the smallest known antigen-binding unit generated by adaptive immune responses (Koch-Nolte F. et al., FASEB J. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_H$-$V_L$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$—$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "fully human" as used herein, with reference to antibody or antigen-binding fragment, means that the antibody or the antigen-binding fragment has or consists of amino acid sequence(s) corresponding to that of an antibody produced by a human or a human immune cell, or derived from a non-human source such as a transgenic non-human animal that utilizes human antibody repertoires or other human antibody-encoding sequences. In certain embodiments, a fully human antibody does not comprise amino acid residues (in particular antigen-binding residues) derived from a non-human antibody.

The term "humanized" as used herein, with reference to antibody or antigen-binding fragment, means that the antibody or the antigen-binding fragment comprises CDRs derived from non-human animals, FR regions derived from human, and when applicable, the constant regions derived from human. A humanized antibody or antigen-binding fragment is useful as human therapeutics in certain embodiments because it has reduced immunogenicity in human. In some embodiments, the non-human animal is a mammal, for example, a mouse, a rat, a rabbit, a goat, a sheep, a guinea pig, or a hamster. In some embodiments, the humanized antibody or antigen-binding fragment is composed of substantially all human sequences except for the CDR sequences which are non-human. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human species, such as from mouse.

"PD-L1" as used herein refers to programmed cell death ligand 1 (PD-L1, see, for example, Freeman et al. (2000) *J. Exp. Med.* 192:1027). Representative amino acid sequence of human PD-L1 is disclosed under the NCBI accession number: NP_054862.1, and the representative nucleic acid sequence encoding the human PD-L1 is shown under the NCBI accession number: NM_014143.3. PD-L1 is expressed in placenta, spleen, lymph nodes, thymus, heart, fetal liver, and is also found on many tumor or cancer cells. PD-L1 binds to its receptor PD-1 or B7-1, which is expressed on activated T cells, B cells and myeloid cells. The binding of PD-L1 and its receptor induces signal transduction to suppress TCR-mediated activation of cytokine production and T cell proliferation. Accordingly, PD-L1 plays a major role in suppressing immune system during particular events such as pregnancy, autoimmune diseases, tissue allografts, and is believed to allow tumor or cancer cells to circumvent the immunological checkpoint and evade the immune response.

"Anti-PD-L1 antibody" as used herein refers to an antibody that is capable of specific binding to PD-L1 (e.g. human or monkey PD-L1) with an affinity which is sufficient to provide for diagnostic and/or therapeutic use.

The term "specific binding" or "specifically binds" as used herein refers to a non-random binding reaction between two molecules, such as for example between an antibody and an antigen. In certain embodiments, the antibodies or antigen-binding fragments provided herein bind specifically to human and/or monkey PD-L1 with a binding affinity ($K_D$) of ≤$10^{-6}$ M (e.g., ≤$5\times10^{-7}$ M, ≤$2\times10^{-7}$ M, ≤$10^{-7}$ M, ≤$5\times10^{-8}$ M, ≤$2\times10^{-8}$ M, ≤$10^{-8}$ M, ≤$5\times10^{-9}$ M, ≤$2\times10^{-9}$ M, ≤$10^{-9}$ M, about $10^{-10}$ M, $10^{-10}$ M to $10^{-9}$ M, $10^{-10}$ M to $10^{-8.5}$ M, or $10^{-10}$ M to $10^{-8}$M). $K_D$ as used herein refers to the ratio of the dissociation rate to the association rate ($k_{off}/k_{on}$), may be determined using surface plasmon resonance methods for example using instrument such as Biacore.

The ability to "block binding" or "compete for the same epitope" as used herein refers to the ability of an antibody or antigen-binding fragment to inhibit the binding interaction between two molecules (e.g. human PD-L1 and an anti-PD-L1 antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein blocks binding of the exemplary antibodies such as 1.4.1, 1.14.4, 1.20.15, and 1.46.11 to human PD-L1, then the antibody or antigen-binding fragment may be considered to bind the same epitope as those exemplary antibodies.

A particular amino acid residue within the epitope can be mutated, e.g. by alanine scanning mutagenesis, and mutations that reduce or prevent protein binding are identified. An "alanine scanning mutagenesis" is a method that can be performed for identifying certain residues or regions of a protein that affect the interaction of the epitope with another compound or protein that binds to it. A residue or group of target residues within the protein is replaced by a neutral or negatively charged amino acid (most preferably alanine or polyalanine, or a conservative amino acid substitution). Any mutation of the amino acid residues or codons encoding the same that reduces binding of the protein more than a threshold or reduces binding of the protein to the maximal degree than other mutations is likely to be within the epitope bound by the protein. In certain embodiments of the present disclosure, the epitope that is critical for the PD-L1 antibody comprises at least one of the amino acid residues of E58, E60, D61, K62, N63 and R113.

"1.4.1" as used herein refers to a fully human monoclonal antibody having a heavy chain variable region of SEQ ID NO: 43, light chain variable region of SEQ ID NO: 45, and a human constant region of IgG4 isotype.

"1.14.4" as used herein refers to a fully human monoclonal antibody having a heavy chain variable region of SEQ ID NO: 47, light chain variable region of SEQ ID NO: 49, and a human constant region of IgG4 isotype.

"1.20.15" as used herein refers to a fully human monoclonal antibody having a heavy chain variable region of SEQ ID NO: 51, light chain variable region of SEQ ID NO: 53, and a human constant region of IgG4 isotype.

"1.46.11" as used herein refers to a fully human monoclonal antibody having a heavy chain variable region of SEQ ID NO: 55, light chain variable region of SEQ ID NO: 49, and a human constant region of IgG4 isotype.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2

(available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"T cell" as used herein includes CD4+ T cells, CD8+ T cells, T helper 1 type T cells, T helper 2 type T cells, T helper 17 type T cells and inhibitory T cells.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. In certain embodiments, the antibodies and antigen-binding fragments have a purity of at least 90%, 93%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced.

A "disease associated with or related to PD-L1" as used herein refers to any condition that is caused by, exacerbated by, or otherwise linked to increased or decreased expression or activities of PD-L1 (e.g. a human PD-L1).

The term "therapeutically effective amount" or "effective dosage" as used herein refers to the dosage or concentration of a drug effective to treat a disease or condition associated with human PD-L1. For example, with regard to the use of the antibodies or antigen-binding fragments disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-PD-L1 Antibody

In one aspect, the present disclosure provides anti-PD-L1 antibodies and the antigen-binding fragments thereof. PD-1, also called as CD279, is known as a key immune-checkpoint receptor expressed by activated T cells, which mediates immunosuppression. PD-1 ligand 1 (PD-L1) is a 40 kDa transmembrane protein expressed on various tumor cells, stromal cells or both, and binds to PD-1. Inhibition of the interaction between PD-1 and PD-L1 can enhance T-cell responses and thus mediates anti-cancer activity.

In certain embodiments, the present disclosure provides exemplary fully human monoclonal antibodies 1.4.1, 1.14.4, 1.20.15, and 1.46.11, whose CDR sequences are shown in the below Table 1, and heavy or light chain variable region sequences are also shown below.

TABLE 1

|  | CDR1 | CDR2 | CDR3 |
| --- | --- | --- | --- |
| 1.4.1-VH (30511) | SEQ ID NO: 1 IRTYYWG | SEQ ID NO: 3 YIYYSGSTRYNPSLKS | SEQ ID NO: 5 LSYFFDY |
|  | SEQ ID NO: 2 ATT AGA ACT TAC TAC TGG GGC | SEQ ID NO: 4 TAT ATC TAT TAT AGT GGG AGC ACC CGC TAC AAC CCG TCC CTC AAG AGT | SEQ ID NO: 6 CTT AGC TAC TTC TTT GAC TAC |

TABLE 1-continued

| | CDR1 | CDR2 | CDR3 |
|---|---|---|---|
| 1.4.1-VL (30027) | SEQ ID NO: 7 SGDKLGDKYAC | SEQ ID NO: 9 QDTKRPS | SEQ ID NO: 11 QAWDSGTVI |
| | SEQ ID NO: 8 TCT GGA GAT AAA TTG GGG GAT AAA TAT GCT TGC | SEQ ID NO: 10 CAA GAT ACC AAG CGG CCC TCA | SEQ ID NO: 12 CAG GCG TGG GAC AGC GGC ACT GTG ATA |
| 1.14.4-VH (29812) | SEQ ID NO: 13 SYAMS | SEQ ID NO: 15 GISGSGGFTYYA DSVKG | SEQ ID NO: 17 PPRGYNYGPFDY |
| | SEQ ID NO: 14 AGC TAT GCC ATG AGT | SEQ ID NO: 16 GGT ATT AGT GGT AGT GGT GGT TTC ACT TAC TAC GCA GAC TCC GTG AAG GGC | SEQ ID NO: 18 CCT CCT CGT GGA TAC AAC TAT GGC CCT TTT GAC TAC |
| 1.14.4-VL (29841) | SEQ ID NO: 19 GGNNIGSKSVH | SEQ ID NO: 21 DDSDRPS | SEQ ID NO: 23 QVWDSSSDHVV |
| | SEQ ID NO: 20 GGG GGA AAC AAC ATT GGA AGT AAA AGT GTA CAC | SEQ ID NO: 22 GAT GAT AGC GAC CGG CCC TCA | SEQ ID NO: 24 CAG GTG TGG GAT AGT AGT AGT GAT CAC GTG GTA |
| 1.20.15-VH (30712) | SEQ ID NO: 25 SISNYWG | SEQ ID NO: 27 SIYYSGSTNYNP PLKS | SEQ ID NO: 29 LTYYFDY |
| | SEQ ID NO: 26 AGT ATT AGT AAC TAC TGG GGC | SEQ ID NO: 28 AGT ATC TAT TAT AGT GGG AGC ACG AAC | SEQ ID NO: 30 CTG ACC TAC TAC TTT GAT TAC |
| | | TAC AAT CCG CCC CTC AAG AGT | |
| 1.20.15-VL (29907) | SEQ ID NO: 31 SGDKLGDKYAC | SEQ ID NO: 33 QDSKRPS | SEQ ID NO: 35 QTWDSSTVV |
| | SEQ ID NO: 32 TCT GGA GAT AAA TTG GGG GAT AAA TAT GCT TGC | SEQ ID NO: 34 CAA GAT AGC AAG CGG CCC TCA | SEQ ID NO: 36 CAG ACG TGG GAC AGC AGC ACT GTG GTA |
| 1.46.11-VH (30626) | SEQ ID NO: 37 SYAMS | SEQ ID NO: 39 GFSGSGFITYYA DSVKG | SEQ ID NO: 41 PPRGYNYGPFDY |
| | SEQ ID NO: 38 AGC TAT GCC ATG AGT | SEQ ID NO: 40 GGT TTT AGT GGT AGT GGT TTT ATT ACA TAC TAC GCA GAC TCC GTG AAG GGC | SEQ ID NO: 42 CCT CCT CGT GGA TAC AAC TAT GGC CCT TTT GAC TAC |
| 1.46.11-VL (29841) | SEQ ID NO: 19 GGNNIGSKSVH | SEQ ID NO: 21 DDSDRPS | SEQ ID NO: 23 QVWDSSSDHVV |
| | SEQ ID NO: 20 GGG GGA AAC AAC ATT GGA AGT AAA AGT GTA CAC | SEQ ID NO: 22 GAT GAT AGC GAC CGG CCC TCA | SEQ ID NO: 24 CAG GTG TGG GAT AGT AGT AGT GAT CAC GTG GTA |

1.4.1-VH(30511): (SEQ ID NO:43 for amino acid and SEQ ID NO:44 for nucleic acid) with heavy chain CDRs 1-3: SEQ ID NOs: 1, 3, 5 are amino acid sequences and SEQ ID NO:2, 4, 6 are nucleic acid sequences, respectively:

```
V segment: IGHV4-39*01
D segment: IGHD1-26*01
J segment: IGHJ4*02
        Q   L   Q   L   Q   E   S   G   P   G   L   V   K   P   S
    1   CAG CTG CAA CTG CAG GAG TCG GGC CCA GGA CTG GTG AAG CCT TCG E   S   L   S   L   T   C   T   V   S   G   G   S   I   S
   46   GAG TCC CTG TCC CTC ACC TGC ACT GTC TCT GGT GGC TCC ATC AGC CDR1
        I   R   T   Y   Y   W   G   W   I   R   Q   P   P   G   T
   91   ATT AGA ACT TAC TAC TGG GGC TGG ATC CGC CAG CCC CCA GGG ACG CDR2
        G   L   E   W   M   G   Y   I   Y   Y   S   G   S   T   R
  136   GGG CTG GAG TGG ATG GGG TAT ATC TAT TAT AGT GGG AGC ACC CGC
                                            CDR2
        Y   N   P   S   L   K   S   R   V   T   I   S   V   D   T
  181   TAC AAC CCG TCC CTC AAG AGT CGA GTC ACC ATA TCC GTA GAC ACG S   K   N   Q   F   S   L   K   L   S   S   V   T   A   A
  226   TCC AAG AAC CAG TTC TCC CTG AAG CTG AGC TCT GTG ACC GCC GCA CDR3
        D   T   A   V   Y   Y   C   A   R   L   S   Y   F   F   D
  271   GAC ACG GCT GTG TAT TAC TGT GCG AGA CTT AGC TAC TTC TTT GAC
                CDR3
        Y   W   G   Q   G   T   L   V   T   V   S   S     (SEQ ID NO: 43)
  316   TAC TGG GGC CAG GGA ACC CTG GTC ACC GTC TCC TCA   (SEQ ID NO: 44)
```

1.4.1-VL(30027): (SEQ ID NO:45 for amino acid and SEQ ID NO:46 for nucleic acid) with light chain CDRs1-3: SEQ ID NOs: 7, 9, 11 are amino acid sequences and SEQ ID NO:8, 10, 12 are nucleic acid sequences, respectively:

```
V segment: IGLV3-1*01
J segment: IGLJ2*01
        S   Y   E   L   T   Q   P   P   S   V   S   V   S   P   G
  1   TCC TAT GAA CTG ACT CAG CCA CCC TCA GTG TCC GTG TCC CCA GGA CDR1
        Q   T   A   S   I   T   C   S   G   D   K   L   G   D   K
 46   CAG ACA GCC AGC ATC ACC TGC TCT GGA GAT AAA TTG GGG GAT AAA CDR1
        Y   A   C   W   Y   Q   Q   K   P   G   Q   S   P   V   M
 91   TAT GCT TGC TGG TAT CAG CAG AAG CCA GGC CAG TCC CCT GTG ATG CDR2
        V   I   Y   Q   D   T   K   R   P   S   G   I   P   E   R
136   GTC ATC TAT CAA GAT ACC AAG CGG CCC TCA GGG ATC CCT GAG CGA F   S   G   S   N   S   G   N   T   A   T   L   T   I   S
181   TTC TCT GGC TCC AAC TCT GGG AAC ACA GCC ACT CTG ACC ATC AGC CDR3
        G   T   L   A   M   D   E   A   D   Y   Y   C   Q   A   W
226   GGG ACC CTG GCT ATG GAT GAG GCT GAC TAT TAT TGT CAG GCG TGG CDR3
        D   S   G   T   V   I   F   G   G   T   K   L   T   V
271   GAC AGC GGC ACT GTG ATA TTC GGC GGA GGG ACC AAG CTG ACC GTC

L   (SEQ ID NO: 45)
316   CTA (SEQ ID NO: 46)
```

1.14.4-VH(29812): (SEQ ID NO:47 for amino acid and SEQ ID NO:48 for nucleic acid) with heavy chain CDRs 1-3: SEQ ID NOs: 13, 15, 17 are amino acid sequences and SEQ ID NO: 14, 16, 18 are nucleic acid sequences, respectively:

```
V segment: IGHV3-23*01
D segment: IGHD5-5*01
J segment: IGHJ4*02
        E   V   Q   L   L   E   S   G   G   G   L   V   Q   P   G
  1   GAG GTG CAA CTG TTG GAG TCT GGG GGA GGC TTG GTA CAG CCT GGG G   S   L   R   L   S   C   A   A   S   F   T   F   S
 46   GGG TCC CTG AGA CTC TCC TGT GCA GCC TCT GGA TTC ACC TTT AGC CDR1
        S   Y   A   M   S   W   V   R   Q   A   P   G   K   G   L
 91   AGC TAT GCC ATG AGT TGG GTC CGC CAG GCT CCA GGG AAG GGG CTG CDR2
        E   W   V   S   G   I   S   G   S   G   F   T   Y   Y
136   GAG TGG GTC TCA GGT ATT AGT GGT AGT GGT GGT TTC ACT TAC TAC CDR2
        A   D   S   V   K   G   R   F   T   I   S   R   D   N   S
181   GCA GAC TCC GTG AAG GGC CGG TTC ACC ATC TCC AGA GAC AAT TCC K   N   T   L   Y   L   Q   M   N   S   L   R   A   E   D
226   AAG AAC ACG CTG TAT CTG CAA ATG AAC AGC CTG AGA GCC GAG GAC CDR3
        T   A   V   Y   Y   C   A   K   P   P   R   G   Y   N   Y
271   ACG GCC GTA TAT TAC TGT GCG AAA CCT CCT CGT GGA TAC AAC TAT CDR3
        G   P   F   D   Y   W   G   Q   G   T   L   V   T   V
316   GGC CCT TTT GAC TAC TGG GGC CAG GGA ACC CTG GTC ACC GTC TCC

S   (SEQ ID NO:47)
361   TCA (SEQ ID NO:48)
```

1.14.4-VL and 1.46.11-VL (29841): (SEQ ID NO:49 for amino acid and SEQ ID NO:50 for nucleic acid) with light chain CDRs 1-3: SEQ ID NOs: 19, 21, 23 are amino acid sequences and SEQ ID NO:20, 22, 24 are nucleic acid sequences, respectively:

```
V segment: IGLV3-21*02
J segment: IGLJ2*01
          S   Y   V   L   T   Q   P   P   S   V   S   V   A   P   G
  1     TCC TAT GTG CTG ACT CAG CCA CCC TCG GTG TCA GTG GCC CCA GGA CDR1
          Q   T   A   R   I   T   C   G   G   N   N   I   G   S   K
 46     CAG ACG GCC AGG ATT ACC TGT GGG GGA AAC AAC ATT GGA AGT AAA CDR1
          S   V   H   W   Y   Q   Q   K   P   G   Q   A   P   V   L
 91     AGT GTA CAC TGG TAC CAG CAG AAG CCA GGC CAG GCC CCT GTG CTG CDR2
          V   V   Y   D   D   S   D   R   P   S   G   I   P   E   R
136     GTC GTC TAT GAT GAT AGC GAC CGG CCC TCA GGG ATC CCT GAG CGA F   S   G   S   N   S   G   N   T   A   L   T   I   S
181     TTC TCT GGC TCC AAC TCT GGG AAC ACG GCC ACC CTG ACC ATC AGC CDR3
          R   V   E   A   G   D   E   A   D   Y   Y   C   Q   V   W
226     AGG GTC GAA GCC GGG GAT GAG GCC GAC TAT TAC TGT CAG GTG TGG CDR3
          D   S   S   S   D   H   V   V   F   G   G   T   K   L
271     GAT AGT AGT AGT GAT CAC GTG GTA TTC GGC GGA GGG ACC AAG CTG

T   V   L   (SEQ ID NO: 49)
316     ACC GTC CTA (SEQ ID NO: 50)
```

1.20.15-VH(30712): (SEQ ID NO:51 for amino acid and SEQ ID NO:52 for nucleic acid) with heavy chain CDRs 1-3: SEQ ID NOs: 25, 27, 29 are amino acid sequences and SEQ ID NO:26, 28, 30 are nucleic acid sequences, respectively:

```
V segment: IGHV4-39*01
D segment: undetermined
J segment: IGHJ4*02
          Q   L   Q   L   Q   E   S   G   P   G   L   V   K   P   S
  1     CAG CTG CAG CTG CAG GAG TCG GGC CCA GGA CTG GTG AAG CCT TCG E   T   L   S   L   T   C   T   V   S   G   G   S   I   S
 46     GAG ACC CTG TCC CTC ACC TGC ACT GTC TCT GGT GGC TCC ATC AGC CDR1
          S   I   S   N   Y   W   G   W   I   R   Q   P   P   G   K
 91     AGT ATT AGT AAC TAC TGG GGC TGG ATC CGC CAG CCC CCA GGG AAG CDR2
          G   L   E   W   I   G   S   I   Y   Y   S   G   S   T   N
136     GGG CTG GAG TGG ATT GGG AGT ATC TAT TAT AGT GGG AGC ACG AAC CDR2
          Y   N   P   P   L   K   S   R   V   T   I   S   V   D   T
181     TAC AAT CCG CCC CTC AAG AGT CGA GTC ACC ATA TCC GTA GAC ACG T   K   N   Q   F   S   L   K   L   S   S   V   T   A   A
226     ACC AAG AAC CAG TTC TCC CTG AAG CTG AGC TCT GTG ACC GCC GCA CDR3
          D   T   A   V   Y   Y   C   A   R   L   T   Y   Y   F   D
271     GAC ACG GCT GTG TAT TAC TGT GCG AGA CTG ACC TAC TAC TTT GAT CDR3
          Y   W   G   Q   G   M   L   V   T   V   S   S   (SEQ ID NO: 51)
316     TAC TGG GGC CAG GGA ATG CTG GTC ACC GTC TCC TCA (SEQ ID NO: 52)
```

1.20.15-VL(29907): (SEQ ID NO:53 for amino acid and SEQ ID NO:54 for nucleic acid) with light chain CDRs 1-3: SEQ ID NOs: 31, 33, 35 are amino acid sequences and SEQ ID NO:32, 34, 36 are nucleic acid sequences, respectively:

```
V segment: IGLV3-1*01
J segment: IGLJ2*01
         S   Y   D   L   T   Q   P   P   S   V   S   V   S   P   G
    1   TCC TAT GAC CTG ACT CAG CCA CCC TCA GTG TCC GTC TCC CCA GGA CDR1
         Q   T   A   S   I   T   C   S   G   D   K   L   G   D   K
   46   CAG ACA GCC AGC ATC ACC TGC TCT GGA GAT AAA TTG GGG GAT AAA CDR1
         Y   A   C   W   Y   Q   Q   K   P   G   Q   S   P   L   L
   91   TAT GCT TGC TGG TAT CAG CAG AAG CCA GGC CAG TCC CCT TTG CTG CDR2
         V   I   Q   Q   D   S   K   R   P   S   G   I   P   A   R
  136   GTC ATC CAG CAA GAT AGC AAG CGG CCC TCA GGG ATC CCT GCG CGA F   S   G   S   N   S   G   N   T   A   T   L   T   I   S
  181   TTC TCT GGC TCC AAC TCT GGG AAC ACA GCC ACT CTG ACC ATC AGC CDR3
         G   T   Q   A   M   D   E   A   D   Y   F   C   Q   T   W
  226   GGG ACC CAG GCT ATG GAT GAG GCT GAC TAT TTC TGT CAG ACG TGG CDR3
         D   S   S   T   V   V   F   G   G   T   K   L   T   V
  271   GAC AGC AGC ACT GTG GTA TTC GGC GGA GGG ACC AAG CTG ACC GTC

L   (SEQ ID NO: 53)
  316   CTA (SEQ ID NO: 54)
```

1.46.11-VH(30626): (SEQ ID NO:55 for amino acid and SEQ ID NO:56 for nucleic acid) with heavy chain CDRs 1-3: SEQ ID NOs: 37, 39, 41 are amino acid sequences and SEQ ID NO:38, 40, 42 are nucleic acid sequences, respectively:

```
V segment: IGHV3-23*01
D segment: IGHD5-5*01
J segment: IGHJ4*02
         E   V   Q   L   L   E   S   G   G   G   L   V   Q   P   G
    1   GAG GTG CAG TTG TTG GAG TCT GGG GGA GGC TTG GTA CAG CCT GGG G   S   L   R   L   S   C   A   A   S   G   F   T   F   S
   46   GGG TCC CTG AGA CTC TCC TGT GCA GCC TCT GGA TTC ACC TTT AGC CDR1
         S   Y   A   M   S   W   V   R   Q   A   P   G   K   G   L
   91   AGC TAT GCC ATG AGT TGG GTC CGC CAG GCT CCA GGG AAG GGG CTG CDR2
         E   W   V   S   G   F   S   G   S   G   F   I   T   Y   Y
  136   GAG TGG GTC TCA GGT TTT AGT GGT AGT GGT TTT ATT ACA TAC TAC CDR2
         A   D   S   V   K   G   R   F   T   I   S   R   D   N   S
  181   GCA GAC TCC GTG AAG GGC CGG TTC ACC ATC TCC AGA GAC AAT TCC K   N   T   L   Y   L   Q   M   N   S   L   R   A   E   D
  226   AAG AAT ACG CTG TAT CTG CAA ATG AAC AGC CTG AGA GCC GAG GAC CDR3
         T   A   V   Y   Y   C   A   M   P   P   R   G   Y   N   Y
  271   ACG GCC GTA TAT TAC TGT GCG ATG CCT CCT CGT GGA TAC AAC TAT CDR3
         G   P   F   D   Y   W   G   Q   G   T   L   V   T   V   S
  316   GGC CCT TTT GAC TAC TGG GGC CAG GGA ACC CTG GTC ACC GTC TCC

S   (SEQ ID NO: 55)
  361   TCA (SEQ ID NO: 56)
```

1.46.11-VL(29841): (SEQ ID NO:49 for amino acid and SEQ ID NO:50 for nucleic acid) with light chain CDRs 1-3: SEQ ID NOs: 19, 21, 23 are amino acid sequences and SEQ ID NO:20, 22, 24 are nucleic acid sequences, respectively:

```
V segment: IGLV3-21*02
J segment: IGLJ2*01
       S   Y   V   L   T   Q   P   P   S   V   S   V   A   P   G
  1   TCC TAT GTG CTG ACT CAG CCA CCC TCG GTG TCA GTG GCC CCA GGA CDR1
       Q   T   A   R   I   T   C   G   G   N   N   I   G   S   K
 46   CAG ACG GCC AGG ATT ACC TGT GGG GGA AAC AAC ATT GGA AGT AAA CDR1
       S   V   H   W   Y   Q   Q   K   P   G   Q   A   P   V   L
 91   AGT GTA CAC TGG TAC CAG CAG AAG CCA GGC CAG GCC CCT GTG CTG CDR2
       V   V   Y   D   D   S   D   R   P   S   G   I   P   E   R
136   GTC GTC TAT GAT GAT AGC GAC CGG CCC TCA GGG ATC CCT GAG CGA F   S   G   S   N   S   G   N   T   A   L   T   I   S
181   TTC TCT GGC TCC AAC TCT GGG AAC ACG GCC ACC CTG ACC ATC AGC CDR3
       R   V   E   A   G   D   E   A   D   Y   Y   C   Q   V   W
226   AGG GTC GAA GCC GGG GAT GAG GCC GAC TAT TAC TGT CAG GTG TGG CDR3
       D   S   S   S   D   H   V   V   F   G   G   T   K   L
271   GAT AGT AGT AGT GAT CAC GTG GTA TTC GGC GGA GGG ACC AAG CTG

T   V   L    (SEQ ID NO: 49)
316   ACC GTC CTA  (SEQ ID NO: 50)
```

In some embodiments, the anti-PD-L1 antibodies and the antigen-binding fragments thereof comprise a heavy chain CDR sequences selected from the group consisting of: SEQ ID NOs: 1, 3, 5, 13, 15, 17, 25, 27, 29, 37, 39 and 41. In some embodiments, the anti-PD-L1 antibodies and the antigen-binding fragments thereof comprise a light chain CDR sequences selected from the group consisting of: SEQ ID NOs: 7, 9, 11, 19, 21, 23, 31, 33, and 35.

In some embodiments, the anti-PD-L1 antibodies and the antigen-binding fragments thereof comprise a heavy chain variable region selected from the group consisting of: a heavy chain variable region comprising SEQ ID NO: 1, SEQ ID NO: 3, and/or SEQ ID NO: 5; a heavy chain variable region comprising SEQ ID NO: 13, SEQ ID NO: 15, and/or SEQ ID NO: 17; a heavy chain variable region comprising SEQ ID NO: 25, SEQ ID NO: 27, and/or SEQ ID NO: 29; and a heavy chain variable region comprising SEQ ID NO: 37, SEQ ID NO: 39, and/or SEQ ID NO: 41.

In some embodiments, the anti-PD-L1 antibodies and the antigen-binding fragments thereof comprise a light chain variable region selected from the group consisting of: a light chain variable region comprising SEQ ID NO: 7, SEQ ID NO: 9, and/or SEQ ID NO: 11; a light chain variable region comprising SEQ ID NO: 19, SEQ ID NO: 21, and/or SEQ ID NO: 23; and a light chain variable region comprising SEQ ID NO: 31, SEQ ID NO: 33, and/or SEQ ID NO: 35.

In some embodiments, the anti-PD-L1 antibodies and the antigen-binding fragments thereof comprising: a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11; b) a heavy chain variable region comprising SEQ ID NO: 13, SEQ ID NO: 15, and/or SEQ ID NO: 17; and a light chain variable region comprising SEQ ID NO: 19, SEQ ID NO: 21, and/or SEQ ID NO: 23; c) a heavy chain variable region comprising SEQ ID NO: 25, SEQ ID NO: 27, and/or SEQ ID NO: 29; and a light chain variable region comprising SEQ ID NO: 31, SEQ ID NO: 33, and/or SEQ ID NO: 35; or d) a heavy chain variable region comprising SEQ ID NO: 37, SEQ ID NO: 39, and/or SEQ ID NO: 41 and a light chain variable region comprising SEQ ID NO: 19, SEQ ID NO: 21, and/or SEQ ID NO: 23.

A skilled artisan will understand that the CDR sequences provided in Table 1 can be modified to contain one or more substitutions of amino acids, so as to provide for an improved biological activity such as improved binding affinity to human PD-L1. For example, a library of antibody variants (such as Fab or scFv variants) can be generated and expressed with phage display technology, and then screened for the binding affinity to human PD-L1. For another example, computer software can be used to virtually simulate the binding of the antibodies to human PD-L1, and identify the amino acid residues on the antibodies which form the binding interface. Such residues may be either avoided in the substitution so as to prevent reduction in binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to human PD-L1 at a level similar to or even higher than its parental antibody having substantially the same sequence except that the corresponding CDR sequence is in 100% sequence identity to that (or those) listed in Table 1.

In certain embodiments, the anti-PD-L1 antibodies and the antigen-binding fragments thereof are fully human. The fully human antibodies do not have the issues of immunogenicity in human and/or reduced binding affinity as often observed with humanized antibodies.

In some embodiments, the fully human anti-PD-L1 antibodies and the antigen-binding fragments thereof comprise a heavy chain variable region selected from the group consisting of: SEQ ID NO: 43, SEQ ID NO: 47, SEQ ID NO: 51, SEQ ID NO: 55, and a homologous sequence thereof having at least 80% (e.g. at least 85%, 88%, 90%, 91%, 92%, 93%, 94%, 95%, 96%, 97%, 98%, 99%) sequence identity; and/or a light chain variable region selected from the group consisting of: SEQ ID NO: 45, SEQ ID NO: 49, SEQ ID NO: 53, and a homologous sequence thereof having at least 80% (e.g. at least 85%, 88%, 90%, 91%, 92%, 93%, 94%, 95%, 96%, 97%, 98%, 99%) sequence identity. Theses fully human antibodies retain the binding affinity to human PD-L1, preferably at a level similar to one of the exemplary antibodies: 1.4.1, 1.14.4, 1.20.15, and 1.46.11.

In some embodiments, the fully human anti-PD-L1 antibodies and the antigen-binding fragments thereof comprise: a) a heavy chain variable region comprising SEQ ID NO: 43; and a light chain variable region comprising SEQ ID NO: 45; b) a heavy chain variable region comprising SEQ ID NO: 47; and a light chain variable region comprising SEQ ID NO: 49; c) a heavy chain variable region comprising SEQ ID NO: 51; and a light chain variable region comprising SEQ ID NO: 53; or d) a heavy chain variable region comprising SEQ ID NO: 55; and a light chain variable region comprising SEQ ID NO: 49.

Also contemplated herein are antibodies and the antigen-binding fragments that compete for the same epitope with the anti-PD-L1 antibodies and the antigen-binding fragments thereof provided herein. In certain embodiments, the antibodies block binding of 1.4.1, 1.14.4, 1.20.15, and 1.46.11 to human or monkey PD-L1, for example, at an $IC_{50}$ value (i.e. 50% inhibition concentration) of below $10^{-6}$ M, below $10^{-7}$ M, below $10^{-7.5}$ M, below $10^{-8}$ M, below $10^{-8.5}$ M, below $10^{-9}$ M, or below $10^{-10}$ M. The $IC_{50}$ values are determined based on a competition assay such as ELISA assays, radioligand competition binding assays, and FACS analysis.

In some embodiments, the anti-PD-L1 antibodies and the antigen-binding fragments thereof provided herein are capable of specifically binding to human PD-L1 with a binding affinity (Kd) of $\leq 10^{-6}$ M (e.g., $\leq 5\times 10^{-7}$ M, $\leq 2\times 10^{-7}$ M, $10^{-7}$ M, $\leq 5\times 10^{-8}$ M, $\leq 2\times 10^{-8}$ M, $\leq 10^{-8}$ M, $\leq 5\times 10^{-9}$ M, $\leq 2\times 10^{-9}$ M, $\leq 10^{-9}$ M, about $10^{-10}$ M, $10^{-10}$ M to $10^{-8.5}$ M, or $10^{-10}$ M to $10^{-8}$ M) as measured by plasmon resonance binding assay. The binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the antibodies and the fragments thereof provided herein binds to human PD-L1 with an $EC_{50}$ (i.e. 50% binding concentration) of 0.1 nM-100 nM (e.g. 0.1 nM-50 nM, 0.1 nM-30 nM, 0.1 nM-20 nM, 0.1 nM-10 nM, or 0.1 nM-1 nM. Binding of the antibodies to human PD-L1 can be measured by methods known in the art, for example, sandwich assay such as ELISA, Western Blot, FACS or other binding assay. In an illustrative example, the test antibody (i.e. first antibody) is allowed to bind to immobilized human PD-L1 or cells expressing human PD-L1, after washing away the unbound antibody, a labeled secondary antibody is introduced which can bind to and thus allow detection of the bound first antibody. The detection can be conducted with a microplate reader when immobilized PD-L1 is used, or by using FACS analysis when cells expressing human PD-L1 are used. In certain embodiments, the antibodies and the fragments thereof provided herein binds to human PD-L1 with an $EC_{50}$ (i.e. 50% effective concentration) of 1 nM to 10 nM, or 1 nM to 5 nM as measured by FACS analysis.

In certain embodiments, the antibodies and the fragments thereof provided herein inhibit the binding of human PD-L1 to its receptor at an $IC_{50}$ of 0.2 nM-100 nM (e.g. 0.2 nM-50 nM, 0.2 nM-30 nM, 0.2 nM-20 nM, 0.2 nM-10 nM or 1 nM-10 nM), as measured in a competition assay.

In certain embodiments, the antibodies and the fragments thereof provided herein block binding of human PD-L1 to its receptor and thereby providing biological activity including, for example, inducing cytokine production from the activated T cells (such as CD4+ T cells and CD8+ T cells), inducing proliferation of activated T cells (such as CD4+ T cells and CD8+ T cells), and reversing T reg's suppressive function. Exemplary cytokines include IL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, CD4$^+$ and CD8$^+$T cells, which is a critical activator of macrophages and inducer of major histocompatibility complex (MHC) molecule expression. The cytokine production can be determined using methods known in the art, for example, by ELISA. Methods can also be used to detect proliferation of T cells, including [$^3$H] thymidine incorporation assay.

The anti-PD-L1 antibodies and the antigen-binding fragments thereof are specific for human PD-L1. In certain embodiments, the antibodies and antigen-binding fragments thereof do not bind to PD-L2 (e.g. human PD-L2). For example, the binding affinity with PD-L2 is less than 15%, 10%, 9%, 8%, 7%, 6%, 5%, 4%, 3%, 2%, or 1% of that with human PD-L1.

In certain embodiments, the antibodies and antigen-binding fragments thereof bind to monkey PD-L1 at an EC50 of no more than 100 nM, for example, no more than or about 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM, as measured by ELISA. In certain embodiments, the antibodies and antigen-binding fragments thereof bind to monkey PD-L1 at an EC50 of about 1 nM-10 nM.

In certain embodiments, the antibodies and antigen-binding fragments thereof do not bind to mouse PD-L1 but bind to monkey PD-L1 with a binding affinity similar to that of human PD-L1. For example, binding of the exemplary antibodies 1.4.1, 1.14.4, 1.20.15, and 1.46.11 to mouse PD-L1 is not detectable in conventional binding assays such as ELISA, or FACS analysis, whereas the binding of these antibodies to monkey PD-L1 is at a similar affinity or EC50 value to that of human PD-L1 as measured by ELISA or FACS.

In some embodiments, the anti-PD-L1 antibodies and the antigen-binding fragments thereof has reduced or depleted effector function. In some embodiments, the anti-PD-L1 antibodies and the antigen-binding fragments thereof have a constant region of IgG4 isotype, which has reduced or depleted effector function. Effector functions such as ADCC and CDC can lead to cytotoxicity to cells expressing PD-L1.

Many cells including normal cells could express PD-L1. In order to avoid potential unwanted toxicity to those normal cells, certain embodiments of the antibodies and antigen-binding fragments provided herein can possess reduced or even depleted effector functions. Various assays are known to evaluate ADCC or CDC activities, for example, Fc receptor binding assay, C1q binding assay, and cell lysis assay, and can be readily selected by people in the art. Without wishing to be bound to theory, but it is believed that antibodies with reduced or depleted effector functions such as ADCC or CDC would cause no or minimal cytotoxicity to PD-L1-expressing cells, for example those normal cells, and therefore spare them from unwanted side effects, whereas in the meantime, tumor cells expressing PD-L1 would be bound by the anti-PD-L1 antibodies and therefore cannot escape from the immune checkpoint and hence can be recognized and eliminated by the immune system.

In certain embodiments, the anti-PD-L1 antibodies and antigen-binding fragments thereof provided herein have reduced side effects. For example, the antibodies and antigen-binding fragments thereof provided herein can have fully human IgG sequence and therefore reduced immunogenicity than a humanized antibody. For another example, the antibodies and antigen-binding fragments thereof provided herein can be in IgG4 format to eliminate ADCC and CDC.

In certain embodiments, the anti-PD-L1 antibodies and antigen-binding fragments thereof provided herein are advantageous in that they can be used in combination with immunogenic agents, such as tumor cells, purified tumor antigen, and cells transfected with genes encoding immune stimulating cytokines, tumor vaccines. In addition, the anti-PD-L1 antibodies and antigen-binding fragments thereof can be included in combination therapies, including standard chemo- and radio-therapies, target based small molecule therapies, emerging other immune checkpoint modulator therapies. In certain embodiments, the antibodies and antigen-binding fragments thereof can be used as the base of antibody-drug conjugates, bispecific or multivalent antibodies.

The anti-PD-L1 antibodies or antigen-binding fragments thereof provided herein can be a monoclonal antibody, polyclonal antibody, fully human antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind two different antigens. An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

In some embodiments, the anti-PD-L1 antibodies or antigen-binding fragments thereof provided herein are fully human antibodies. In certain embodiments, the fully human antibodies are prepared using recombinant methods. For example, transgenic animal such as a mouse can be made to carry transgenes or transchromosomes of human immunoglobulin genes, and therefore capable of producing fully human antibodies after immunization with proper antigen such as human PD-L1. Fully human antibodies can be isolated from such transgenic animal, or alternatively, can be made by hybridoma technology by fusing the spleen cells of the transgenic animal with an immortal cell line to generate hybridoma cells secreting the fully human antibodies. Exemplary transgenic animals include, without limitation, OmniRat, whose endogenous expression of rat immunoglobulin genes are inactivated and at the same time engineered to contain functional recombinant human immunoglobulin loci; OmniMouse, whose endogenous expression of mouse immunoglobulin genes are inactivated and at the same time engineered to contain recombinant human immunoglobulin loci having J-locus deletion and a C-kappa mutation; OmniFlic, which is a transgenic rat whose endogenous expression of rat immunoglobulin genes are inactivated and at the same time engineered to contain recombinant human immunoglobulin loci having a single common, rearranged VkJk light chain and functional heavy chain. Detailed information can be further found at: Osborn M. et al, Journal of Immunology, 2013, 190: 1481-90; Ma B. et al, Journal of Immunological Methods 400-401 (2013) 78-86; Geurts A. et al, Science, 2009, 325:433; U.S. Pat. No. 8,907,157; EP patent 2152880B1; EP patent 2336329B1, all of which are incorporated herein by reference to its entirety. Other suitable transgenic animals can also be used, for example, HuMab mice (see, for details, Lonberg, N. et al. Nature 368(6474): 856 859 (1994)), Xeno-Mouse (Mendez et al. Nat Genet., 1997, 15:146-156), TransChromo Mouse (Ishida et al. Cloning Stem Cells, 2002, 4:91-102) and VelocImmune Mouse (Murphy et al. Proc Natl Acad Sci USA, 2014, 111:5153-5158), Kymouse (Lee et al. Nat Biotechnol, 2014, 32:356-363), and transgenic rabbit (Flisikowska et al. PLoS One, 2011, 6:e21045).

In some embodiments, the anti-PD-L1 antibodies and the antigen-binding fragments thereof is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In some embodiments, the anti-PD-L1 antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues.

In some embodiments, the anti-PD-L1 antibodies and the antigen-binding fragments thereof further comprise a conjugate. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin. The conjugate can be a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides, luminescent labels), chromophoric moiety, digoxigenin, biotin/avidin, a DNA molecule or gold for detection. In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the conjugate can be a purification moiety such as a magnetic bead. A "cytotoxic moiety" can be any agent that is detrimental to cells or that can damage or kill cells. Examples of cytotoxic moiety include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Polynucleotides and Recombinant Methods

The present disclosure provides isolated polynucleotides that encode the anti-PD-L1 antibodies and the antigen-binding fragments thereof. In certain embodiments, the isolated polynucleotides comprise one or more nucleotide sequences as shown in Table 1, which encodes the CDR sequences provided in Table 1.

In some embodiments, the isolated polynucleotides encodes a heavy chain variable region and comprise a sequence selected from the group consisting of: SEQ ID NO: 44, SEQ ID NO: 48, SEQ ID NO: 52, SEQ ID NO: 56, and a homologous sequence thereof having at least 80% (e.g. at least 85%, 88%, 90%, 91%, 92%, 93%, 94%, 95%, 96%, 97%, 98%, 99%) sequence identity. In some embodiments, the isolated polynucleotides encodes a light chain variable region and comprise a sequence selected from the group consisting of: SEQ ID NO: 46, SEQ ID NO: 50, SEQ ID NO: 54, and a homologous sequence thereof having at least 80% (e.g. at least 85%, 88%, 90%, 91%, 92%, 93%, 94%, 95%, 96%, 97%, 98%, 99%) sequence identity. In certain embodiments, the percentage identity is due to genetic code degeneracy, while the encoded protein sequence remains unchanged.

The isolated polynucleotide that encodes the anti-PD-L1 antibodies and the antigen-binding fragments thereof (e.g. including the sequences in Table 1) can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, plS5TV-L, pPro18, pTD, pRS420, pLexA, pACT2.2 etc, and other laboratorial and commercially available vectors. Suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-PD-L1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruifly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of Spodoptera frugiperda cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-PD-L1 antibody production and cultured in conventional nutrient media modified as appropriate for inducing promoters, selecting transformants, or amplifying the genes encoding the desired sequences.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure provides kits comprising the anti-PD-L1 antibodies or the antigen-binding fragments thereof. In some embodiments, the kits are useful for detecting the presence or level of PD-L1 in a biological sample. The biological sample can comprise a cell or a tissue.

In some embodiments, the kit comprises an anti-PD-L1 antibody or the antigen-binding fragment thereof which is conjugated with a detectable label. In certain other embodiments, the kit comprises an unlabeled anti-PD-L1 antibody or antigen-binding fragment, and further comprises a secondary labeled antibody which is capable of binding to the unlabeled anti-PD-L1 antibody. The kit may further comprise an instruction of use, and a package that separates each of the components in the kit.

In certain embodiments, the anti-PD-L1 antibody or the antigen-binding fragment thereof are associated with a substrate or a device useful in a sandwich assay such as ELISA, or in an immunographic assay. Useful substrate or device can be, for example, microtiter plate and test strip.

Pharmaceutical Composition and Method of Treatment

The present disclosure further provides pharmaceutical compositions comprising the anti-PD-L1 antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcellulose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-PD-L1 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods are also provided, comprising: administering a therapeutically effective amount of the antibody or antigen-binding fragment as provided herein to a subject in need thereof, thereby treating or preventing a condition or a disorder associated with related to PD-L1. In another aspect, methods are provided to treat a condition in a subject that would benefit from upregulation of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Conditions and disorders associated with PD-L1 can be immune related disease or disorder. In certain embodiments, the PD-L1 associated conditions and disorders include, tumors and cancers, for example, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially metastatic tumors expressing PD-L1. In certain embodiments, the PD-L1 associated conditions and disorders include autoimmune diseases, such as systemic lupus erythematosus (SLE), psoriasis, systemic scleroderma, autoimmune diabetes and the like, In certain embodiments, the PD-L1 associated conditions and disorders include infectious disease such as chronic viral infection for example, viral infection of hepatitis B, hepatitis C, herpes virus, Epstein-Barr virus, HIV, cytomegalovirus, herpes simplex virus type I, herpes simplex virus type 2, human papilloma virus, adenovirus, Kaposi West sarcoma associated herpes virus epidemics, thin ring virus (Torquetenovirus), JC virus or BK virus.

Methods of Use

The present disclosure further provides methods of using the anti-PD-L1 antibodies or the antigen-binding fragments thereof.

In some embodiments, the present disclosure provides methods of treating a condition or a disorder associated with related to PD-L1 in an individual, comprising administering a therapeutically effective amount of the anti-PD-L1 antibody or antigen-binding fragment thereof. In certain embodiments, the individual has been identified as having a disorder or condition likely to respond to a PD-L1 antagonist.

The presence or level of PD-L1 on an interested biological sample can be indicative of whether the individual from whom the biological sample is derived could likely respond to a PD-L1 antagonist. Various methods can be used to determine the presence or level of PD-L1 in a test biological sample from the individual. For example, the test biological sample can be exposed to anti-PD-L1 antibody or antigen-binding fragment thereof, which binds to and detects the expressed PD-L1 protein. Alternatively, PD-L1 can also be detected at nucleic acid expression level, using methods such as qPCR, reverse transcriptase PCR, microarray, SAGE, FISH, and the like. In some embodiments, the test sample is derived from a cancer cell or tissue, or tumor infiltrating immune cells. In certain embodiments, presence or upregulated level of the PD-L1 in the test biological sample indicates likelihood of responsiveness. The term "upregulated" as used herein, refers to an overall increase of no less than 10%, 15%, 20%, 25%, 30%, 35%, 40%, 45%, 50%, 55%, 60%, 65%, 70%, 75%, 80% or greater, in the protein level of PD-L1 in the test sample as detected using the antibodies or antigen-binding fragments provided herein, as compared to the PD-L1 protein level in a reference sample as detected using the same antibody. The reference sample can be a control sample obtained from a healthy or non-diseased individual, or a healthy or non-diseased sample obtained from the same individual from whom the test sample is obtained. For example, the reference sample can be a non-diseased sample adjacent to or in the neighborhood of the test sample (e.g. tumor).

The antibodies or antigen-binding fragments disclosed herein may be administered alone or in combination with one or more additional therapeutic means or agents. For example, the antibodies or antigen-binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for use in the treatment of cancer or any medical disorder mediated by PD-L1. In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

In certain embodiments, the therapeutic agents can induce or boost immune response against cancer. For example, a tumor vaccine can be used to induce immune response to certain tumor or cancer. Cytokine therapy can also be used to enhance tumor antigen presentation to the immune system. Examples of cytokine therapy include, without limitation, interferons such as interferon-α, -β, and -γ, colony stimulating factors such as macrophage-CSF, granulocyte macrophage CSF, and granulocyte-CSF, interleukins such IL-1, IL-1α, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets can also be used, for example, TGF-beta inhibitors, IL-10 inhibitors, and Fas ligand inhibitors. Another group of agents include those that activate immune responsiveness to tumor or cancer cells, for example, those enhance T cell activation (e.g. agonist of T cell costimulatory molecules such as CTLA-4, ICOS and OX-40), and those enhance dendritic cell function and antigen presentation.

The present disclosure further provides methods of monitoring therapeutic response or disease progression in a subject treated with PD-L1 antagonist, comprising determining presence or level of PD-L1 in a test biological sample from the individual with the anti-PD-L1 antibody or antigen-binding fragment thereof. In certain embodiments, the methods further comprise comparing the PD-L1 level in the test biological sample with the PD-L1 level in a comparable sample previously obtained from the same individual, wherein reduction, or slowed or halted increase in the PD-L1 level in the test biological sample indicates positive therapeutic response or controlled disease progression. The comparable sample can be the same type of sample as the test sample, but has been obtained from the same individual before treatment, or during an earlier stage of the treatment.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Antibody Hybridoma Generation 1.1 Immunization: female OMT rats (obtained from Open Monoclonal Technology, Inc., Palo Alto, US, 8-10 weeks of age), were primed with 10 μg of human PD-L1 ECD protein in TiterMax via footpad injection, and then boosted every 3 days with PD-L1 ECD protein in Aluminium Phosphate Gel Adjuvant via footpad injection, until ready for fusion. Anti-PD-L1 antibody serum titers were examined by ELISA or FACS every other week.

1.2 Cell fusion: Three days prior to fusion, animals received a final boost with 10 μg of human PD-L1 ECD protein in PBS through intraperitoneal injection. On the day of fusion, lymph nodes were harvested and prepared to get single cell suspension. Obtained lymphocytes were mixed with myeloma cells (P3) at proper ratio. Cell mixture was washed and re-suspended at $2.0 \times 10^6$ cells/mL in ECF solution. The fusion was performed by using the BTX 2000 electricity instrument.

1.3 Primary and secondary screen of hybridoma supernatants: after culturing for 7-14 days at 37° C., a portion of the hybridoma supernatant was examined by using Mirrorball analysis. Briefly, the hybridoma supernatant was diluted 5 times in 1×PBS. PD-L1 expressing CHO-K1 cells were mixed with the secondary fluorochrome labeled antibody and DraQ5. In each well of the 384-well plate, 20 μL of the cell mixture and 20 μL of the diluted hybridoma supernatant sample were added and incubated for at least 2 hours at room temperature in the dark, until ready for analysis on a Mirrorball® high sensitivity microplate cytometer. The positive hits were confirmed by FACS using the PD-L1 expressing CHO-K1 cells. The cells were stained with the hybridoma supernatant samples, followed by 2nd antibody staining with FITC conjugated Goat Anti-Mouse IgG Fc. Corresponding parental cell lines were used as negative controls. The stained cells were analyzed by using a BD Biosciences FACSCanto II and FlowJo Version software.

1.4 Subclone: the hybridoma cell lines with confirmed positive binding to PD-L1 expressing cells were used for subcloning. Briefly, for each hybridoma cell line, cells were counted and diluted to give 5 or 1 cells per 200 μL in cloning medium. Plate 200 μL/well into the 96-well plates. Plates were incubated at 37° C., 5% $CO_2$ until ready for following analysis.

1.5 Isotype test: the ELISA plates were coated with 50 μL/well of goat anti-rat IgG1, IgG2a, IgG2b, IgG3, IgA and IgM antibodies at 1 μg/mL, respectively. After blocking, 50 μL of hybridoma supernatant samples were added into each well, and incubated at room temperature for 2 hours. The goat anti-rat kappa light chain-HRP was used as the detecting antibody. The color reaction was developed using TMB substrate for 10 minutes, and stopped by 2M HCl. The plates were then read at 450 nm on an ELISA microplate reader.

1.6 Cell based binding assay: To examine the binding activity of the fully human antibodies to target, CHO-K1 cells that express human PD-L1 or mature dendritic cells (mDCs) were stained with the fully human antibodies, followed by $2^{nd}$ antibody staining with FITC conjugated goat anti-human IgG Fc. Corresponding parental cell lines were used as negative controls. The stained cells were analyzed by using a BD Biosciences FACSCanto II and FlowJo Version software.

The CHO cells transfected with full-length human PD-L1 were stained with antibodies against human PD-L1 from rat hybridoma, followed by 2$^{nd}$ antibody staining with FITC conjugated goat anti-rat IgG Fc and analyzed by FACS. As shown in FIG. 1, antibodies 1.4.1, 1.14.4, 1.20.15 and 1.46.11 specifically bound to PD-L1 expressed on CHO cells with EC50 values of about 1 nM.

Example 2: Change Fc Portion and Purification

The antibodies in the 293F cell culture supernatant were then purified by using the protein A affinity chromatography.

Example 3: Fully Human Antibody Characterization 3.1 Competition assay by FACS: to examine whether the fully human antibodies can block the binding of PD-L1 to PD-1, the CHO-K1 cells expressing human PD-L1 were incubated with various concentrations of the fully human antibodies at 4° C. for 1 hour. The unbound antibodies were washed away, and then the mouse Fc-tagged human PD-1 was added to the cells. The binding of human PD-1 to PD-L1 expressing cell was detected by using FITC-conjugated goat anti-mouse IgG, followed by the analysis using a BD Biosciences FACSCanto II and FlowJo Version software.

Figure 2:
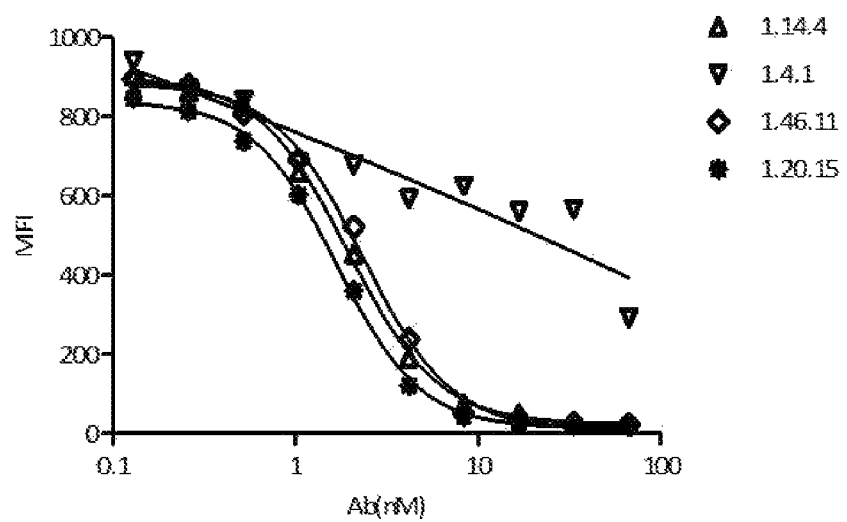
FIG. 2 presents the fully human PD-L1 antibodies blocked the binding of PD-1 to PD-L1 transfected CHO cells as measured by FACS analysis.

CHO cells expressing human PD-L1 were incubated with different concentrations of the fully human antibodies (1.4.1, 1.14.4, 1.20.15 and 1.46.11). Then the mouse Fc-tagged human PD-1 was added to the cells. The binding of human PD-1 to PD-L1 expressing cell was detected by using FITC-conjugated goat anti-mouse IgG, followed by the FACS analysis. As shown in FIG. 2, all the tested fully human PD-L1 antibodies blocked the PD-1 binding to PD-L1 expressed on transfected CHO cells, and 1.14.4, 1.20.15 and 1.46.11 showed an IC 50 value of about 10 nM.

3.2 Affinity test by surface plasmon resonance (SPR): Antibodies were characterized for affinity and binding kinetics to PD-L1 by SPR assay using ProteOn XPR36 (Bio-Rad). Protein A protein (Sigma) was immobilized to a GLM sensor chip (Bio-Rad) through amine coupling. Purified antibodies were flowed over the sensor chip and captured by the Protein A. The chip was rotated 90° and washed with running buffer (1×PBS/0.01% Tween20, Bio-Rad) until the baseline is stable. Five concentrations of human PD-L1 and running buffer were flowed against the antibody flow cell at a flow rate 100 μL/min for an association phase of 240 s, followed by 600 s dissociation. The chip was regenerated with pH 1.7 $H_3PO_4$ after each run. The association and dissociation curve was fit to a 1:1 Langmiur binding model using ProteOn software.

Figures 5, 6:
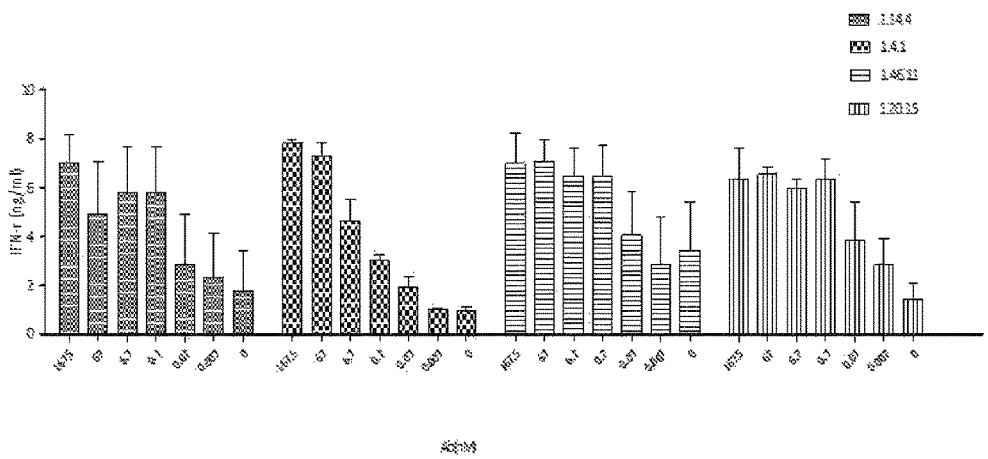
FIG. 5 is the full kinetics of binding affinity of PD-L1 antibodies to human PD-L1 ranging from 2.26E-10 to 4.78E-10 mol/L as determined by surface plasmon resonance.
FIG. 6 illustrates the effect of fully human anti-PD-L1 antibodies on IFNγ production in specific T cell response.

As shown in FIG. 5, the affinities of fully human PD-L1 antibodies for recombinant human PD-L1 were from 4.78E-10 to 2.26E-10 mol/L, as measured by surface plasmon resonance.

3.3 Affinity test by FACS: antibody binding affinity to cell surface PD-L1 was performed by FACS analysis using CHO-K1 cells expressing human PD-L1. Tested antibodies were 1 in 2 serially diluted in wash buffer (1×PBS/1% BSA) and incubated with cells at 4° C. for 1 h. The secondary antibody goat anti-human IgG Fc FITC (Jackson Immunoresearch Lab) was added and incubated at 4° C. in the dark for 1 h. The cells were then washed once and resuspended in 1×PBS/1% BSA, and analyzed by flow cytometery (BD). Fluorescence intensity will be converted to bound molecules/cell based on the quantitative beads Quantum™ MESF Kits (Bangs Laboratories, Inc.). KD was calculated using Graphpad Prism5.

3.4 In vitro functional assay: to evaluate the ability of the fully human antibodies in modulating T cell responsiveness, including the cytokine production and cell proliferation, following three assays were performed.

3.4.1 Allogeneic MLR: monocytes were isolated from healthy donors using Human Monocyte Enrichment kit according to the manufacturer's instruction. Cells were cultured for 5-7 days to differentiate into dendritic cells (DCs). 18 to 24 hours before usage, 1 μg/ml LPS was added to the cell culture to induce the maturation of the DCs.

CD4$^+$ T cells were isolated using Human CD4$^+$ T Cell Enrichment kit according to the manufacturer's protocol, and then were stimulated with the mature or immature allogenenic DCs in the presence or absence of fully human antibodies or control Ab. The levels of IL-2 and IFNγ in the culture supernatant were measured by ELISA on Day 3 and Day 5, respectively. The proliferation of CD4$^+$ T cells were assessed by [$^3$H] thymidine incorporation.

Figure 8:
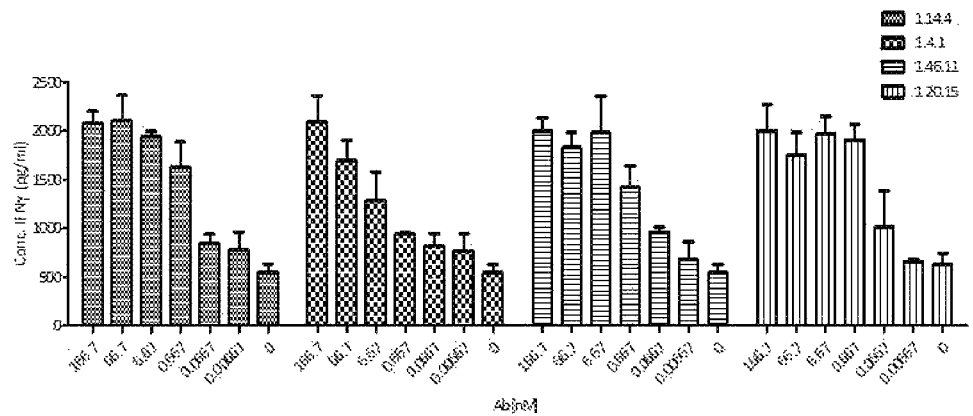
FIG. 8 shows that fully human PD-L1 antibodies enhanced IFNγ production in mixed lymphocyte reaction (MLR).
Figure 9:
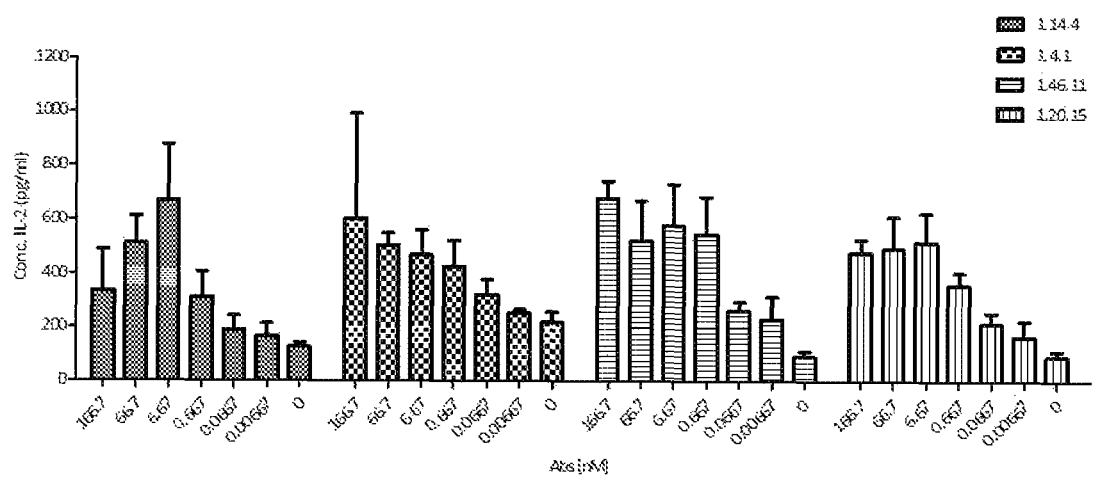
FIG. 9 illustrates the effect of fully human anti-PD-L1 antibodies on IL-2 production in MLR.
Figure 10:
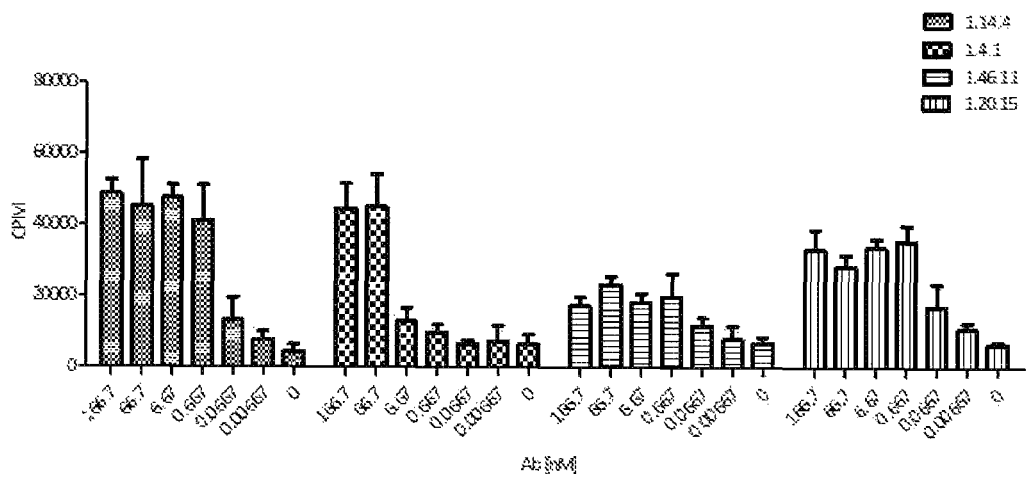
FIG. 10 shows that anti-PD-L1 antibodies promoted T cell proliferation in MLR.

As shown in FIG. 9, all the tested fully human PD-L1 antibodies (1.4.1, 1.14.4, 1.20.15 and 1.46.11) increased IL-2 secretion in a dose manner. As shown in FIG. 8, all the tested fully human PD-L1 antibodies (1.4.1, 1.14.4, 1.20.15 and 1.46.11) increased IFNγ secretion in a dose manner. As shown in FIG. 10, all the tested fully human PD-L1 antibodies (1.4.1, 1.14.4, 1.20.15 and 1.46.11) enhanced concentration dependent T cell proliferation.

3.4.2 Autologous Ag-specific immune response: PBMC and monocytes were isolated from the same donor. PBMC were cultured in the presence of CMV pp65 peptide and low dose of IL2 (20 U/ml). At the meantime, DCs were generated by culturing monocytes as previously mentioned. After 5 days, the DCs were pulsed with pp65 peptide and then added to the CD4$^+$ T cells in the presence or absence of the fully human antibodies or control Ab. The levels of IL-2 and IFNγ in the culture supernatant were measured by ELISA on Day 3 and Day 5, respectively. The proliferation of CMVpp65-specific CD4$^+$ T cells were assessed by [$^3$H] thymidine incorporation.

Figure 7:
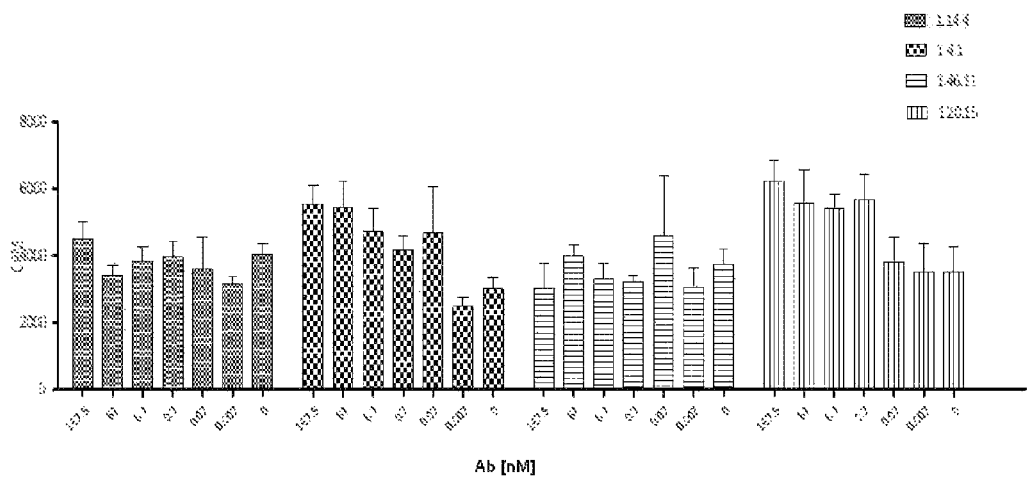
FIG. 7 shows that fully human anti-PD-L1 antibodies enhanced specific T cell proliferation.

As shown in FIG. 6, the IFNγ production in specific T cell response was enhanced by the fully human PD-L1 antibodies (1.4.1, 1.14.4, 1.20.15 and 1.46.11). FIG. 7 shows that fully human PD-L1 antibodies enhanced concentration dependent CMV$^+$-CD4$^+$ T cell proliferation stimulated with CMV pp65 peptide-loaded autologous DCs.

3.4.3 Treg suppression assay: regulatory T cells (Tregs) are a key immune modulator and play key roles in maintaining self-tolerance. CD4$^+$CD25$^+$ Tregs are associated with tumors because increased numbers of Tregs were found in patients with multiple cancers and are associated with a poorer prognosis. To directly assess the effect of anti-human PD-L1 fully human antibodies on Tregs' inhibitory function, we compared the Treg's function in the presence or absence of fully human antibodies or control Ab. Briefly, CD4$^+$CD25$^+$ Tregs and CD4$^+$CD25$^-$ T cells were separated by MACS. CD4$^+$CD25$^+$ Tregs and CD4$^+$CD25$^-$ T cells (Treg: Teff 1:1 ratio) were co-cultured with allogeneic mDCs in the presence or absence of the fully human antibodies or control Ab at different concentrations. Either no antibody or isotype antibody was used as negative control. The cytokine production and T cell proliferation were measured as previously mentioned.

Figure 11:
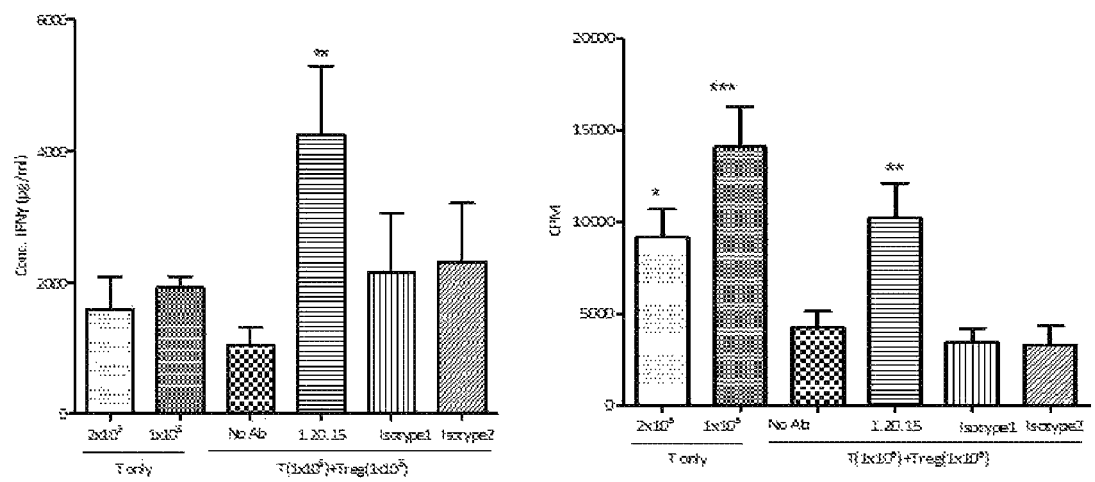
FIG. 11 shows that anti-PD-L1 antibodies reversed Treg's suppressive function.

As shown in FIG. 11, PD-L1 antibody 1.20.15 abrogated Treg's suppressive function and restored responding T cell proliferation and IFNγ secretion.

3.5 Antibody-dependent cell-mediated cytoxicity (ADCC) and complement-dependent cytoxicity (CDC) assay: as the human PD-L1 is expressed in a variety of cell types, and on both healthy and tumor cells, to minimize the undesired toxicity on healthy PD-L1+ cells, the selected anti-PD-L1 fully human antibodies were confirmed to have no ADCC and CDC function.

3.5.1 ADCC: target cells (mDCs) and various concentrations of fully human antibodies were pre-incubated in 96-well plates for 30 min, then IL-2 activated PBMCs (effector) were added at the effector/target ratio of 50:1. The plates were incubated for 6 hours at 37° C. in a 5% $CO_2$ incubator. Target cell lysis was determined by cytotoxicity detection kit (Roche). Optical density was measured by Molecular Devices SpectraMax M5e Plate Reader. Control hAb (IgG1) and control hAb (IgG4) were used as positive and negative controls, respectively.

Figure 12:
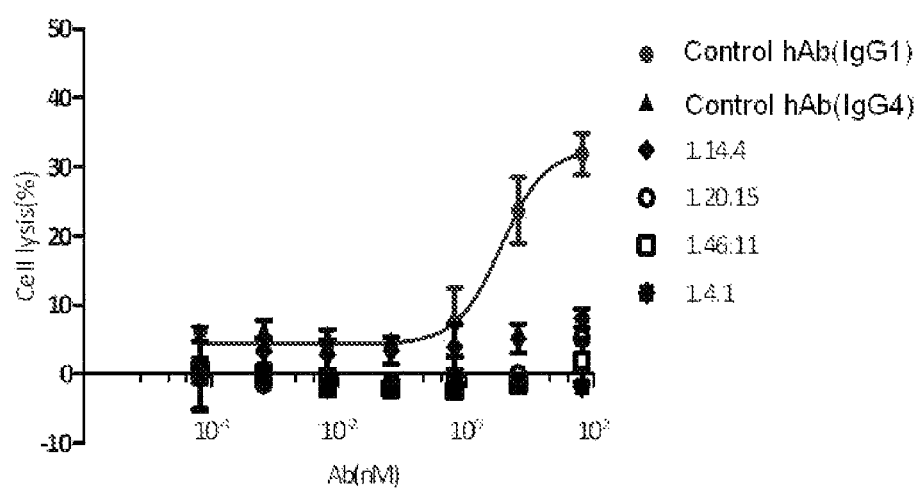
FIG. 12 shows the anti-PD-L1 antibodies lacked ADCC on activated T cells.

Using IL-2-activated PBMCs as a source of natural killer (NK) cells and mDC expressing high levels of cell surface PD-L1 as target cells, fully human PD-L1 antibodies (1.4.1, 1.14.4, 1.20.15 and 1.46.11) did not mediate ADCC (FIG. 12).

Figure 13:
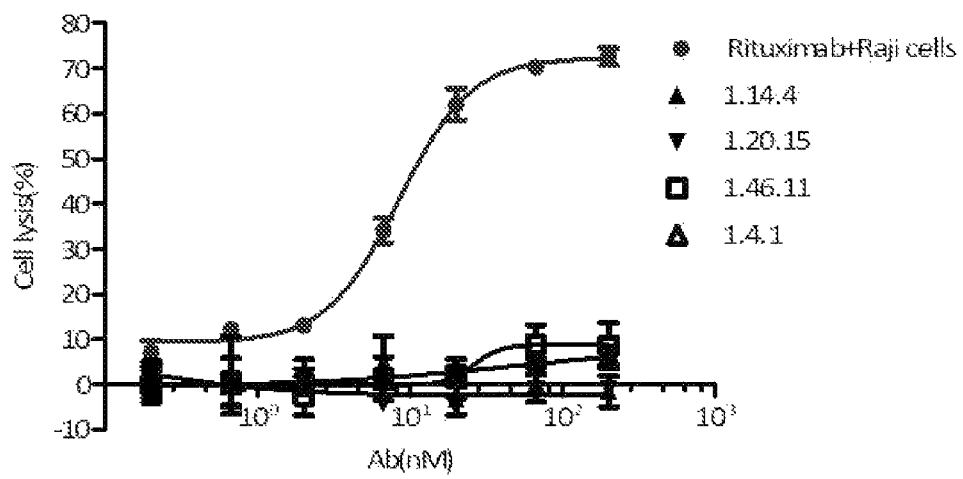
FIG. 13 shows the anti-PD-L1 antibodies lacked CDC on activated T cells.

3.5.2 CDC: target cells (mDC), diluted human serum complement (Quidel-A112) and various concentrations of fully human antibodies were mixed in a 96-well plate. The plate was incubated for 4 h at 37° C. in a 5% $CO_2$ incubator. Target cell lysis was determined by CellTiter glo (Promega-G7573). Rituxan (Roche) and human B lymphoma cell line Raji (CD20 positive) were used as positive control. As shown in FIG. 13, fully human PD-L1 antibodies did not mediated CDC.

3.6 Binning test by FACS: To examine whether the fully human antibodies were in the same epitope bin as the benchmark antibody, the CHO-K1 cells expressing human PD-L1 were incubated with different concentrations of the fully human antibodies at 4° C. for 1 hour. The unbound antibodies were washed away, and then the biotin-tagged control Ab was added to the cells. The binding of the biotin-tagged control Ab to the PD-L1 expressing cells was detected by using PE-conjugated streptavidin, followed by the analysis using a BD Biosciences FACSCanto II and FlowJo Version software.

The results for the binning test showed that the epitope on human PD-L1 bound by the fully human PD-L1 antibodies (i.e. 1.4.1, 1.14.4, 1.20.15 and 1.46.11) was different from the existing PD-L1 antibodies (i.e. benchmark antibody).

3.7 Cross-species binding assay: the cross-reactivity of the Ab to cynomolgus and murine PD-L1 was measured by ELISA. Human, cyno and mouse PD-L1 were coated on ELISA plates, respectively. After blocking, fully human antibodies were added into the plate and incubated at room temperature for at least 2 hours. The binding of the antibodies to the coated antigens was detected by using goat anti-human IgG Fc-HRP. The color reaction was developed using TMB substrate and stopped by 2M HCl. The ELISA plates were analyzed at 450 nm using a Molecular Device M5e microplate reader.

Figure 4:
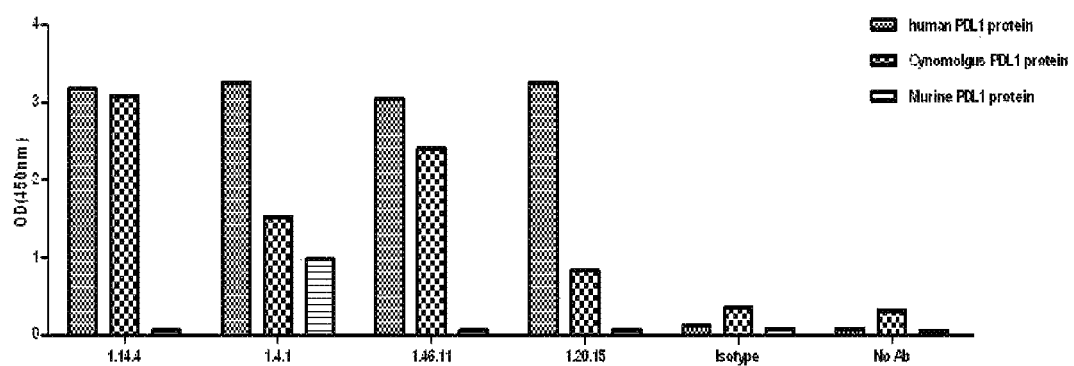
FIG. 4 shows that the fully human PD-L1 antibodies bound to human and cynomolgus monkey PD-L1.

As shown in FIG. 4, the result of ELISA experiment demonstrated that the tested fully human PD-L1 bound to cynomolgus monkey PD-L1 in a dose dependent manner. However, none of the tested antibodies (1.4.1, 1.14.4, 1.20.15 and 1.46.11) bound to murine PD-L1.

3.8 Cross-family binding assay by FACS: to examine the cross-family binding activity of the fully human antibodies, cells lines that express PD-L2 were stained with the fully human antibodies, followed by $2^{nd}$ antibody staining with FITC conjugated goat anti-human IgG Fc. PD-L1 expressing cells were used as positive control. Corresponding parental cell lines were used as negative controls. The stained cells were analyzed by using a BD Biosciences FACSCanto II and FlowJo Version software.

Figure 3:
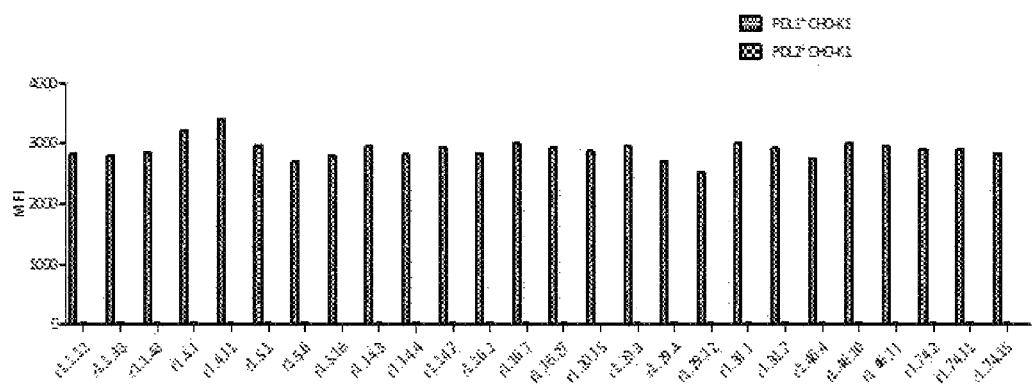
FIG. 3 shows that the fully human PD-L1 antibodies specifically bound to PD-L1, but did not bind to PD-L2, as measured by FACS analysis.

CHO cells transfected with PD-L1 or PD-L2 were stained with fully human PD-L1 antibodies and analysis by FACS. As shown in FIG. 3, the fully human PD-L1 antibodies bound specifically to PD-L1, but not to PD-L2 of PD-1 ligand family.

Example 4: Epitope Mapping of the Fully Human Antibody

To determine the epitopes the present antibody 1.14.4 provided herein, alanine scanning experiments on hPD-1 and the effect evaluation to antibody binding were conducted using 1.14.4.

Alanine scanning experiments on hPD-L1 were conducted and their effect to antibody binding was evaluated. Alanine residues on hPD-L1 were mutated to glycine codons, and all other residues were mutated to alanine codons. For each residue of the hPD-L1 extracellular domain (ECD), point amino acid substitutions were made using two sequential PCR steps. A pcDNA3.3-hPD-L1_ECD.His plasmid that encodes ECD of human PD-L1 and a C-terminal His-tag was used as template, and a set of mutagenic primer was used for first step PCR using the QuikChange lightning multi site-directed mutagenesis kit (Agilent technologies, Palo Alto, Calif.). Dpn I endonuclease was used to digest the parental template after mutant strand synthesis reaction. In the second-step PCR, linear DNA expression cassette which composed of a CMV promoter, an extracellular domain (ECD) of PD-L1, a His-tag and a herpes simplex virus thymidine kinase (TK) polyadenylation was amplified and transiently expressed in HEK293F cells (Life Technologies, Gaithersburg, Md.).

Monoclonal antibody 1.14.4 was coated in plates for ELISA binding assay. After interacting with the supernatant that contains quantified PD-L1 mutant or human/mouse PD-L1_ECD.His protein (Sino Biological, China), HRP conjugated anti-His antibody (1:5000; Rockland Immunochemicals, Pottstown, Pa.) was added as detection antibody. Absorbance was normalized according to the average of control mutants. After setting an additional cutoff to the binding fold change (<0.55), the final determined epitope residues were identified.

Figure 14A:
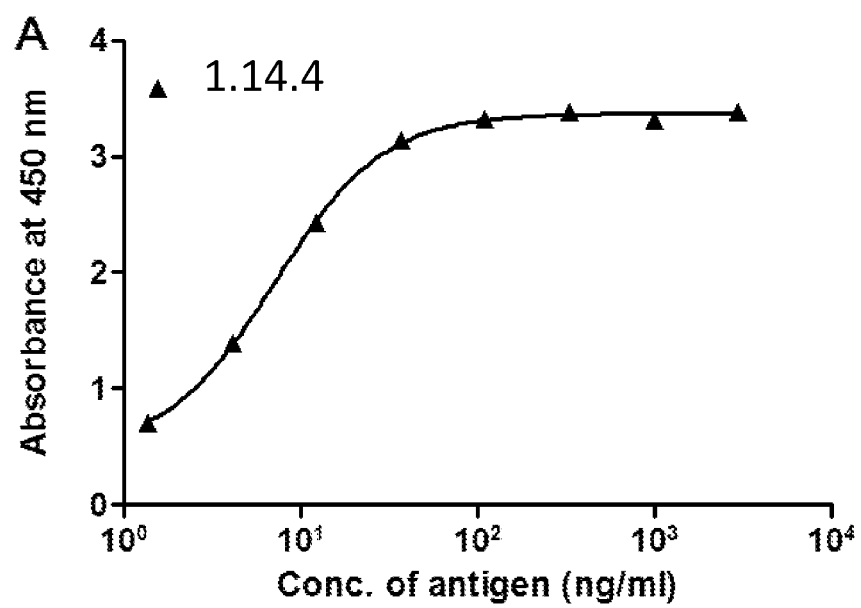
FIGS. 14A and 14B show cross-reactivity of anti-PD-L1 antibodies with human/mouse PD-1. 2 μg/ml of 1.14.4 antibody was coated at 96-well plate overnight and incubated with (FIG. 14A) hPD-L1-His protein and (FIG. 14B) mPD-L1-His protein, then HRP-anti-His antibody were added for detection.
Figure 14B:
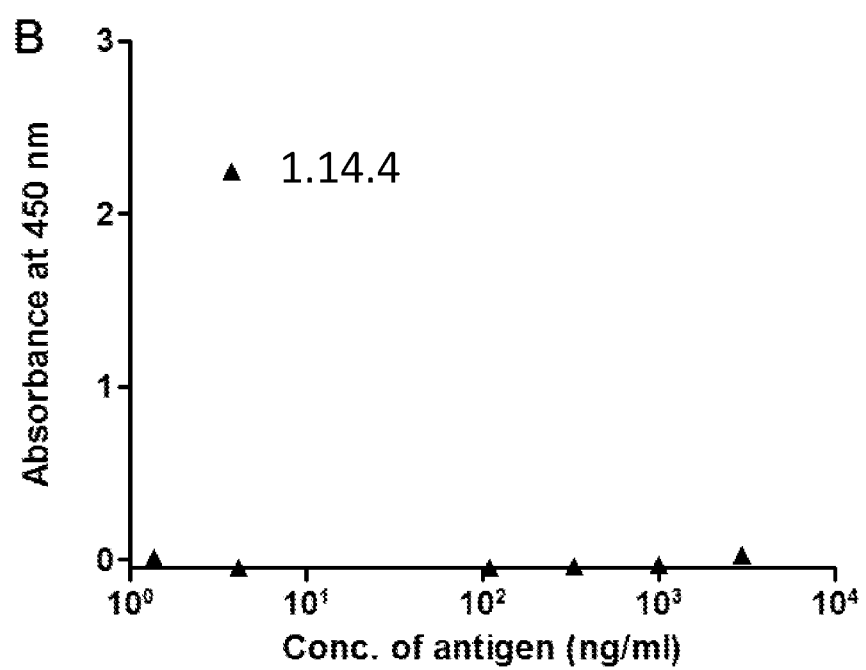

The binding activities of the antibodies 1.14.4 to both human and murine PD-L1 were conducted (FIG. 14). Our lead 1.14.4 was found binding to human PD-L1 (FIG. 14A), but no bound to mouse PD-L1 (FIG. 14B).

The effect of 131 PD-L1 point mutations on antibody binding was shown in Table 2. Checking the positions of all these residues on the hPD-L1 crystal structures (PDB code 3BIK and 4ZQK) revealed that some amino acids (e.g. Gly159, Tyr160, Pro161) were unlikely to directly contact any antibodies. The observed binding reductions most probably resulted from the instability or even collapse of hPD-L1 structure after alanine substitutions. After setting an additional cutoff to the binding fold change (<0.55), the final determined epitope residues were listed in Table 3. They are 6 positions to 1.14.4.

Figure 15:
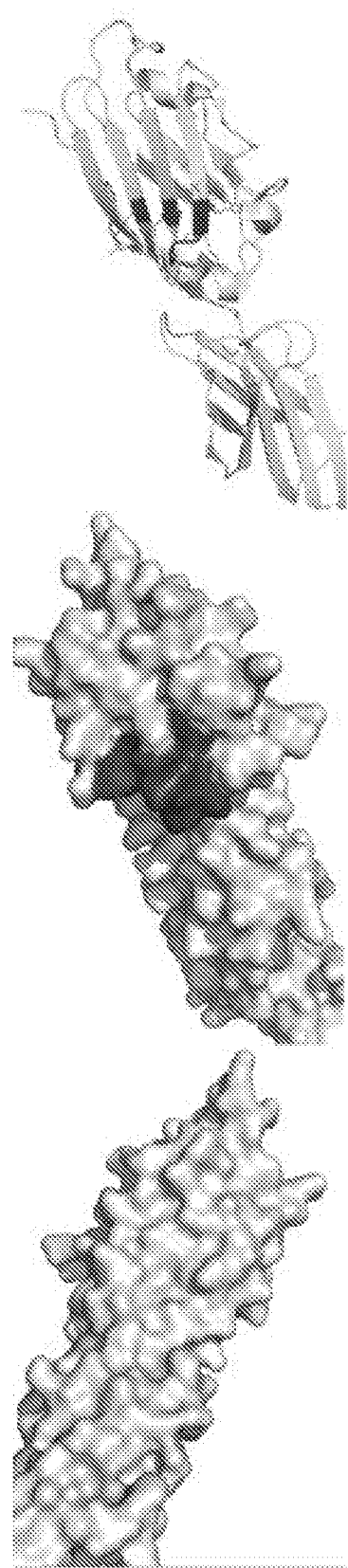
FIG. 15 shows hot spot residues mapped on hPD-L1 structure. Binding site of antibody 1.14.4. Data were from table 3. Colors on the pictures are to help distinguish the differences between epitopes.

All data in Table 3 were therefore mapped on the crystal structure of hPD-L1 to make a better visualization and comparison. (FIG. 15).

TABLE 2

The effect of PD-L1 point mutations on antibody binding 1.14.4

| PD-L1 | #Residue | fold change [a] | SD |
|---|---|---|---|
| R | 113 | 0.161 | 0.000 |
| K | 62 | 0.169 | 0.004 |
| N | 63 | 0.285 | 0.008 |
| P | 161 | 0.332 | 0.011 |
| D | 61 | 0.372 | 0.002 |
| E | 58 | 0.399 | 0.004 |
| G | 159 | 0.448 | 0.017 |
| Y | 160 | 0.505 | 0.024 |
| E | 60 | 0.547 | 0.004 |
| P | 216 | 0.563 | 0.017 |
| T | 37 | 0.569 | 0.004 |
| K | 129 | 0.586 | 0.011 |
| G | 70 | 0.602 | 0.019 |
| D | 49 | 0.603 | 0.002 |
| L | 50 | 0.614 | 0.005 |
| A | 52 | 0.622 | 0.010 |
| G | 110 | 0.632 | 0.000 |
| P | 133 | 0.664 | 0.007 |
| G | 95 | 0.668 | 0.016 |
| N | 131 | 0.680 | 0.000 |
| Y | 81 | 0.692 | 0.007 |
| Y | 118 | 0.701 | 0.005 |
| V | 128 | 0.701 | 0.012 |
| V | 68 | 0.707 | 0.012 |
| I | 64 | 0.716 | 0.009 |
| V | 111 | 0.723 | 0.003 |
| L | 106 | 0.732 | 0.008 |
| E | 218 | 0.732 | 0.000 |
| T | 127 | 0.735 | 0.021 |
| E | 72 | 0.748 | 0.025 |
| V | 225 | 0.749 | 0.048 |
| A | 232 | 0.756 | 0.010 |
| K | 189 | 0.759 | 0.021 |
| V | 76 | 0.760 | 0.010 |
| L | 48 | 0.770 | 0.006 |
| E | 71 | 0.772 | 0.012 |
| F | 19 | 0.780 | 0.045 |
| T | 201 | 0.781 | 0.012 |
| N | 35 | 0.788 | 0.003 |
| Q | 107 | 0.792 | 0.001 |
| A | 109 | 0.797 | 0.004 |
| E | 205 | 0.801 | 0.010 |
| V | 21 | 0.803 | 0.011 |
| R | 186 | 0.805 | 0.008 |
| G | 33 | 0.807 | 0.000 |
| D | 215 | 0.811 | 0.015 |
| S | 34 | 0.813 | 0.006 |
| K | 105 | 0.816 | 0.004 |
| H | 78 | 0.821 | 0.006 |
| E | 217 | 0.823 | 0.136 |
| G | 119 | 0.825 | 0.010 |
| E | 39 | 0.831 | 0.002 |
| E | 188 | 0.833 | 0.000 |
| P | 43 | 0.834 | 0.010 |
| V | 44 | 0.837 | 0.001 |
| L | 231 | 0.838 | 0.003 |
| Y | 56 | 0.840 | 0.002 |
| Y | 28 | 0.842 | 0.015 |
| L | 175 | 0.842 | 0.009 |
| N | 236 | 0.848 | 0.019 |
| I | 199 | 0.848 | 0.011 |
| K | 185 | 0.853 | 0.003 |
| K | 25 | 0.857 | 0.080 |
| D | 90 | 0.858 | 0.003 |
| D | 103 | 0.863 | 0.007 |
| T | 203 | 0.870 | 0.015 |
| R | 212 | 0.870 | 0.006 |
| T | 22 | 0.875 | 0.004 |
| I | 206 | 0.876 | 0.002 |
| V | 29 | 0.882 | 0.001 |
| T | 102 | 0.887 | 0.001 |
| T | 154 | 0.888 | 0.004 |
| T | 179 | 0.893 | 0.030 |
| G | 120 | 0.895 | 0.007 |
| F | 191 | 0.897 | 0.021 |
| T | 196 | 0.898 | 0.049 |
| Q | 91 | 0.906 | 0.016 |
| P | 24 | 0.907 | 0.009 |
| E | 31 | 0.908 | 0.033 |
| K | 89 | 0.913 | 0.009 |
| I | 54 | 0.918 | 0.045 |
| N | 96 | 0.924 | 0.007 |
| R | 82 | 0.934 | 0.003 |
| Y | 32 | 0.935 | 0.009 |
| S | 117 | 0.935 | 0.010 |
| S | 169 | 0.939 | 0.018 |
| E | 45 | 0.942 | 0.002 |
| N | 183 | 0.944 | 0.021 |
| T | 181 | 0.947 | 0.038 |
| V | 23 | 0.948 | 0.019 |
| L | 27 | 0.949 | 0.001 |
| E | 237 | 0.956 | 0.001 |
| L | 214 | 0.958 | 0.013 |
| R | 125 | 0.959 | 0.009 |
| S | 79 | 0.962 | 0.007 |
| D | 26 | 0.963 | 0.010 |
| T | 20 | 0.974 | 0.017 |
| S | 80 | 0.974 | 0.015 |
| Q | 66 | 0.979 | 0.016 |
| A | 18 | 0.979 | 0.011 |
| Q | 83 | 0.982 | 0.003 |
| V | 174 | 0.983 | 0.009 |
| D | 73 | 0.988 | 0.014 |
| K | 162 | 0.990 | 0.008 |
| T | 180 | 1.000 | 0.025 |
| R | 86 | 1.001 | 0.003 |
| A | 98 | 1.009 | 0.002 |
| Q | 77 | 1.011 | 0.002 |
| M | 59 | 1.012 | 0.006 |
| Q | 100 | 1.012 | 0.002 |
| K | 75 | 1.015 | 0.021 |
| M | 115 | 1.016 | 0.040 |
| V | 143 | 1.016 | 0.031 |
| V | 147 | 1.017 | 0.005 |
| L | 74 | 1.021 | 0.018 |
| N | 135 | 1.026 | 0.130 |
| A | 51 | 1.035 | 0.037 |
| M | 36 | 1.036 | 0.005 |
| L | 142 | 1.047 | 0.072 |
| Q | 47 | 1.051 | 0.030 |
| K | 124 | 1.056 | 0.004 |
| H | 69 | 1.056 | 0.003 |
| K | 41 | 1.071 | 0.036 |
| K | 46 | 1.085 | 0.029 |
| L | 88 | 1.102 | 0.017 |
| Y | 123 | 1.108 | 0.005 |
| I | 38 | 1.132 | 0.026 |
| S | 93 | 1.145 | 0.024 |
| A | 121 | 1.147 | 0.018 |
| L | 94 | 1.189 | 0.021 |
| D | 122 | 1.215 | 0.026 |

[a] Fold change in binding is relative to the binding of several silent alanine substitutions.

TABLE 3

Identification of potential epitopes

| PD-L1 to 1.14.4 | residue location |
|---|---|
| E 58 | C strand |
| E 60 | C strand |
| D 61 | C strand |
| K 62 | CC' loop |
| N 63 | CC' loop |
| R 113 | F strand |

Cutoff: fold change < 0.55

As shown in FIG. 15, the hot-spot residues in charge of the hPD-L1 binding all gathered in the C strand, CC' loop and F strands (FIG. 15). Checking the positions of the residues on the hPD-1/hPD-L1 complex crystal structures (PDB code 4ZQK, 4 Å) revealed that these residues mainly located on A, C, F and G strands. The epitopes of 1.14.4 was mainly contributed by the residues on the C strands, which have direct overlap with the hPD-1 and hPD-L1 interaction site, indicating the mechanisms in terms of hPD-L1 binding and hPD-1 blocking.

Example 5: In Vivo Inhibition of Fully Human Antibody hPD-L1 to the Tumor Growth In order to assess the inhibition of hPD-L1 antibody to the tumor growth, $5 \times 10^5$ cells/0.1 mL of MC38-B7H1 tumor cells were inoculated subcutaneously to the anterior right rib of 42 male B-hPD-1 humanized mice. When the tumor size reached about 100 mm$^3$, the mice were grouped (5 groups, 7 per group) and administered with agents as follows: Group 1: vehicle, Group 2: control antibody BMK6 (see detailed description in WO2011066389A1), Group 3: 1.14.4, 3 mg/kg, Group 4: 1.14.4, 10 mg/kg and Group 5: 1.14.4, 30 mg/kg. All groups were administered via intraperitoneal injection once every two days with six consecutive administration. The animals were continually observed for another two weeks after the end of administration. The tumor volume and body weight were measured twice a week, and the relationships between the change of mouse body weight and period of administration, and the change of tumor volume and period of administration were recorded. At the end of the experiment, the ratio of the tumor volumes in therapeutic groups to vehicle group (T/C) and tumor growth inhibition (TGI) were calculated and analyzed statistically. T-test was performed with Graphpad Prism 5 and tumor volume was analyzed statistically. P<0.05 was considered to have significant difference.

Tumor volume was measured twice a week using vernier caliper for the long diameter and short diameter, and the formula for calculating the volume is: Tumor volume=0.5× long diameter×short diameter$^2$. Tumor growth rate was calculated based on the measuring results: T/C (%)=tumor volume of therapeutic group/tumor volume of negative control group×100%. Tumor growth inhibition TGI (%)= [1−(Ti−T0)/(Vi−V0)]×100, wherein Ti is the average tumor volume of the therapeutic group at day i, T0 is the average tumor volume of the therapeutic group at day 0, Vi is the average tumor volume of the control group at day i, and V0 is the average tumor volume of the control group at day 0.

TABLE 4

Anti-tumor effects of fully human PD-L1 antibody 1.14.4 to MC38-B7H1 xenograft of murine colon cancer hPD-1 humanized mice.

| Group | Number of animals | Body weight (g) $^a$ Before administration | Body weight (g) $^a$ After Administration | Tumor volume after 25 days of inculation (mm$^3$) | T/C (%) after 25 days of inculation | Tumor growth inhibition TGI (%) | P$^b$ |
|---|---|---|---|---|---|---|---|
| Group1: Vehicle | 7 | 27.6 ± 1.3 | 28.8 ± 1.5 | 2359 | — | — | — |
| Group 2: BMK6 | 7 | 28.3 ± 0.5 | 29.3 ± 0.7 | 1241 | 52.6% | 49.7% | 0.02 |
| Group 3: 1.14.4, 3 mg/kg | 7 | 28.0 ± 0.5 | 29.7 ± 0.5 | 949 | 40.2% | 62.8% | 0.02 |
| Group 4: 1.14.4, 10 mg/kg | 7 | 27.8 ± 0.8 | 30.3 ± 1.1 | 1416 | 60.0% | 42.0% | 0.09 |
| Group 5: 1.14.4, 30 mg/kg | 7 | 26.7 ± 0.9 | 27.5 ± 1.0 | 1115 | 47.3% | 55.4% | 0.04 |

Notes:
$^a$ mean ± SE;
$^b$ in comparison to control

Figure 16:
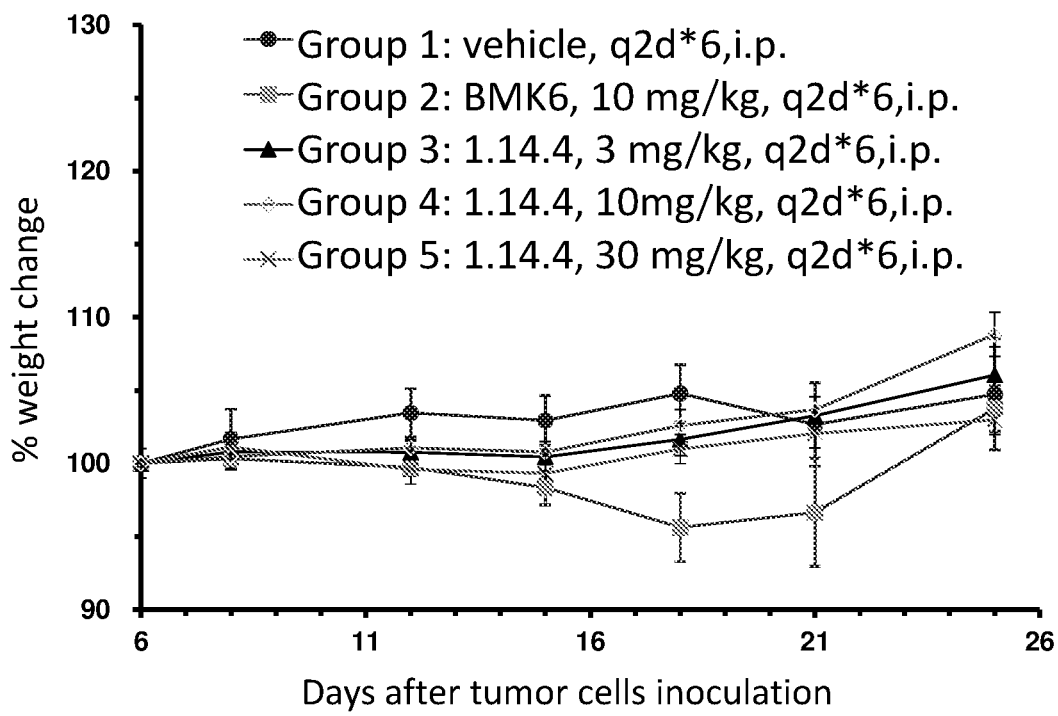
FIG. 16 shows good in vivo tolerability of the hPD-L1 antibody 1.14.4. Three doses of antibody 1.14.4 (3 mg/kg, 10 mg/kg and 30 mg/kg) were administered via multi intraperitoneal injections to the humanized B-hPD-1 mouse. No significant change of the body weight was observed during the experiment.
Figure 17:
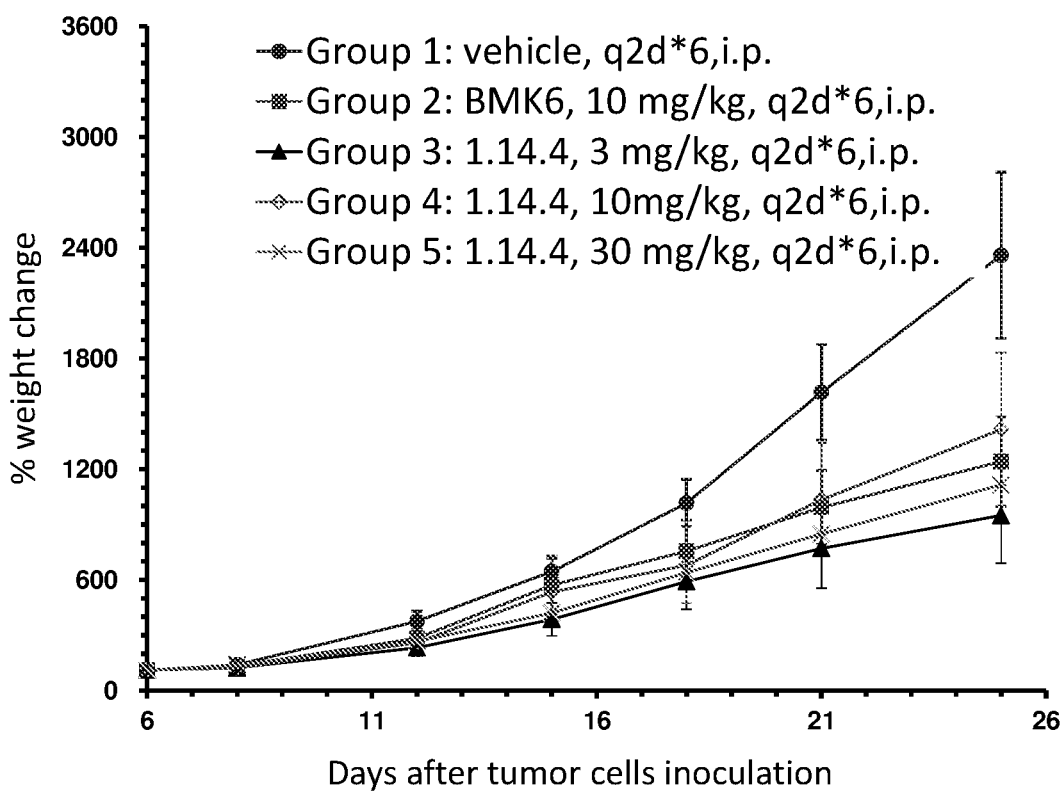
FIG. 17 shows significant in vivo inhibition of the hPD-L1 antibody 1.14.4 to the tumor cell growth. After 19 days of antibody administration, all the three doses of antibody 1.14.4 (3 mg/kg, 10 mg/kg and 30 mg/kg) showed significant anti-tumor effects indicated by tumor growth inhibitions (TGI) of >40%.

During the experiment, the body weight of the animals in each group did not show significant decrease (Table 4 and FIG. 16), indicating that the test agents have good tolerability. After the 19 days of administration (i.e. 25 days after tumor cells inoculation), the tumor volume in the vehicle group reached 2359 mm$^3$, and compared with the vehicle group, the tumor volumes in the groups of high, mediate and low doses of antibody 1.14.4 showed significant decrease (average tumor volume were 949 mm$^3$, 1416 mm$^3$ and 1115 mm$^3$, respectively). All the three doses of antibody showed significant anti-tumor effects indicating by the TGI 62.8%, 42.0% and 55.4%, respectively (Table 4 and FIG. 17). The control antibody BMK6 also showed significant anti-tumor effect (average tumor volume is 1241 mm$^3$, and TGI is 49.7%). Therefore, results showed that antibody 1.14.4 showed significant anti-tumor effect, and the inhibitions for all the groups of high, mediate and low doses were above 40%.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. An isolated anti-PD-L1 antibody or an antigen binding fragment, comprising:
   a) a heavy chain variable region comprising SEQ ID NO: 1, SEQ ID NO: 3, and SEQ ID NO: 5; and a light chain variable region comprising SEQ ID NO: 7, SEQ ID NO: 9, and SEQ ID NO: 11;
   b) a heavy chain variable region comprising SEQ ID NO: 13, SEQ ID NO: 15, and SEQ ID NO: 17; a light chain variable region comprising SEQ ID NO: 19, SEQ ID NO: 21, and SEQ ID NO: 23;
   c) a heavy chain variable region comprising SEQ ID NO: 25, SEQ ID NO: 27, and SEQ ID NO: 29; a light chain variable region comprising SEQ ID NO: 31, SEQ ID NO: 33, and SEQ ID NO: 35; or
   d) a heavy chain variable region comprising SEQ ID NO: 37, SEQ ID NO: 39, and SEQ ID NO: 41, and a light chain variable region comprising SEQ ID NO: 19, SEQ ID NO: 21, and SEQ ID NO: 23.

2. The antibody or an antigen binding fragment thereof of claim 1, comprising a heavy chain variable region selected from the group consisting of: SEQ ID NO: 43, SEQ ID NO: 47, SEQ ID NO: 51 and SEQ ID NO: 55.

3. The antibody or an antigen binding fragment thereof of claim 1, comprising a light chain variable region selected from the group consisting of: SEQ ID NO: 45, SEQ ID NO: 49 and SEQ ID NO: 53.

4. The antibody or an antigen binding fragment thereof of claim 1, comprising:
   a) a heavy chain variable region comprising SEQ ID NO: 43; and a light chain variable region comprising SEQ ID NO: 45;
   b) a heavy chain variable region comprising SEQ ID NO: 47; and a light chain variable region comprising SEQ ID NO: 49;
   c) a heavy chain variable region comprising SEQ ID NO: 51; and a light chain variable region comprising SEQ ID NO: 53; or d) a heavy chain variable region comprising SEQ ID NO: 55; and a light chain variable region comprising SEQ ID NO: 49.

5. The antibody or an antigen binding fragment thereof of claim 1, capable of specifically binding to human PD-L1 at an Kd value no more than $10^{-8}$ M as measured by plasmon resonance binding assay.

6. The antibody or an antigen binding fragment thereof of claim 1, which binds to monkey PD-L1 at an EC50 of no more than 1 OnM, or no more than 1 nM, and/or does not bind to mouse PD-L1.

7. The antibody or an antigen binding fragment thereof of claim 1, capable of inhibiting binding of human or monkey PD-L1 to its receptor at an IC50 of no more than 100 nM.

8. The antibody or an antigen binding fragment thereof of claim 1, which does not substantially bind to PD-L2.

9. The antibody or an antigen binding fragment thereof of claim 1, which does not mediate ADCC or CDC or both.

10. The antibody or an antigen binding fragment thereof of claim 1, which is a fully human monoclonal antibody.

11. The antibody or an antigen binding fragment thereof of claim 10, wherein the fully human monoclonal antibody is produced by a transgenic rat.

12. The antibody or an antigen binding fragment thereof of claim 1, capable of blocking binding of human PD-L1 to its receptor and thereby providing at least one of the following activities:
   a) inducing production of IL-2 in $CD4^+$ T cells;
   b) inducing production of IFNγ in $CD4^+$ T cells;
   c) inducing proliferation of $CD4^+$ T cells; and
   d) reversing T reg's suppressive function.

13. The antibody or antigen-binding fragment thereof of claim 1, which is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

14. The antibody or antigen-binding fragment thereof of claim 1, further comprising an immunoglobulin constant region.

15. The antibody or antigen-binding fragment thereof of claim 1, further comprising a conjugate.

16. A kit comprising the antibody or antigen-binding fragment thereof of claim 1.

17. A pharmaceutical composition comprising the antibody or antigen-binding fragment thereof of claim 1 and one or more pharmaceutically acceptable carriers.

* * * * *

SEQUENCE LISTING

<160> NUMBER OF SEQ ID NOS: 56

<210> SEQ ID NO 1
<211> LENGTH: 7
<212> TYPE: PRT
<213> ORGANISM: Homo sapiens

<400> SEQUENCE: 1

Ile Arg Thr Tyr Tyr Trp Gly
1               5

<210> SEQ ID NO 2
<211> LENGTH: 21
<212> TYPE: DNA
<213> ORGANISM: Homo sapiens

<400> SEQUENCE: 2
attagaactt actactgggg c                                              21

<210> SEQ ID NO 3
<211> LENGTH: 16
<212> TYPE: PRT
<213> ORGANISM: Homo sapiens

<400> SEQUENCE: 3

Tyr Ile Tyr Tyr Ser Gly Ser Thr Arg Tyr Asn Pro Ser Leu Lys Ser
1               5                   10                  15

<210> SEQ ID NO 4
<211> LENGTH: 48
<212> TYPE: DNA
<213> ORGANISM: Homo sapiens

<400> SEQUENCE: 4
tatatctatt atagtgggag cacccgctac aacccgtccc tcaagagt                 48

<210> SEQ ID NO 5
<211> LENGTH: 7
<212> TYPE: PRT
<213> ORGANISM: Homo sapiens

<400> SEQUENCE: 5

Leu Ser Tyr Phe Phe Asp Tyr
1               5

<210> SEQ ID NO 6
<211> LENGTH: 21
<212> TYPE: DNA
<213> ORGANISM: Homo sapiens

<400> SEQUENCE: 6
cttagctact tctttgacta c                                              21

<210> SEQ ID NO 7
<211> LENGTH: 11
<212> TYPE: PRT
<213> ORGANISM: Homo sapiens

<400> SEQUENCE: 7

Ser Gly Asp Lys Leu Gly Asp Lys Tyr Ala Cys
1               5                   10

<210> SEQ ID NO 8
<211> LENGTH: 33

```
<212> TYPE: DNA
<213> ORGANISM: Homo sapiens

<400> SEQUENCE: 8
tctggagata aattgggga taaatatgct tgc                           33

<210> SEQ ID NO 9
<211> LENGTH: 7
<212> TYPE: PRT
<213> ORGANISM: Homo sapiens

<400> SEQUENCE: 9

Gln Asp Thr Lys Arg Pro Ser
1               5

<210> SEQ ID NO 10
<211> LENGTH: 21
<212> TYPE: DNA
<213> ORGANISM: Homo sapiens

<400> SEQUENCE: 10
caagatacca agcggccctc a                                       21

<210> SEQ ID NO 11
<211> LENGTH: 9
<212> TYPE: PRT
<213> ORGANISM: Homo sapiens

<400> SEQUENCE: 11

Gln Ala Trp Asp Ser Gly Thr Val Ile
1               5

<210> SEQ ID NO 12
<211> LENGTH: 27
<212> TYPE: DNA
<213> ORGANISM: Homo sapiens

<400> SEQUENCE: 12
caggcgtggg acagcggcac tgtgata                                 27

<210> SEQ ID NO 13
<211> LENGTH: 5
<212> TYPE: PRT
<213> ORGANISM: Homo sapiens

<400> SEQUENCE: 13

Ser Tyr Ala Met Ser
1               5

<210> SEQ ID NO 14
<211> LENGTH: 15
<212> TYPE: DNA
<213> ORGANISM: Homo sapiens

<400> SEQUENCE: 14
agctatgcca tgagt                                              15

<210> SEQ ID NO 15
<211> LENGTH: 17
<212> TYPE: PRT
<213> ORGANISM: Homo sapiens

<400> SEQUENCE: 15

Gly Ile Ser Gly Ser Gly Gly Phe Thr Tyr Tyr Ala Asp Ser Val Lys
```

Gly

<210> SEQ ID NO 16
<211> LENGTH: 51
<212> TYPE: DNA
<213> ORGANISM: Homo sapiens

<400> SEQUENCE: 16
ggtattagtg gtagtggtgg tttcacttac tacgcagact ccgtgaaggg c        51

<210> SEQ ID NO 17
<211> LENGTH: 12
<212> TYPE: PRT
<213> ORGANISM: Homo sapiens

<400> SEQUENCE: 17

Pro Pro Arg Gly Tyr Asn Tyr Gly Pro Phe Asp Tyr
1               5                   10

<210> SEQ ID NO 18
<211> LENGTH: 36
<212> TYPE: DNA
<213> ORGANISM: Homo sapiens

<400> SEQUENCE: 18
cctcctcgtg gatacaacta tggcccttttt gactac        36

<210> SEQ ID NO 19
<211> LENGTH: 11
<212> TYPE: PRT
<213> ORGANISM: Homo sapiens

<400> SEQUENCE: 19

Gly Gly Asn Asn Ile Gly Ser Lys Ser Val His
1               5                   10

<210> SEQ ID NO 20
<211> LENGTH: 33
<212> TYPE: DNA
<213> ORGANISM: Homo sapiens

<400> SEQUENCE: 20
gggggaaaca acattggaag taaaagtgta cac        33

<210> SEQ ID NO 21
<211> LENGTH: 7
<212> TYPE: PRT
<213> ORGANISM: Homo sapiens

<400> SEQUENCE: 21

Asp Asp Ser Asp Arg Pro Ser
1               5

<210> SEQ ID NO 22
<211> LENGTH: 21
<212> TYPE: DNA
<213> ORGANISM: Homo sapiens

<400> SEQUENCE: 22
gatgatagcg accggccctc a        21

<210> SEQ ID NO 23

```
<211> LENGTH: 11
<212> TYPE: PRT
<213> ORGANISM: Homo sapiens

<400> SEQUENCE: 23

Gln Val Trp Asp Ser Ser Asp His Val Val
1               5                   10

<210> SEQ ID NO 24
<211> LENGTH: 33
<212> TYPE: DNA
<213> ORGANISM: Homo sapiens

<400> SEQUENCE: 24
caggtgtggg atagtagtag tgatcacgtg gta                                    33

<210> SEQ ID NO 25
<211> LENGTH: 7
<212> TYPE: PRT
<213> ORGANISM: Homo sapiens

<400> SEQUENCE: 25

Ser Ile Ser Asn Tyr Trp Gly
1               5

<210> SEQ ID NO 26
<211> LENGTH: 21
<212> TYPE: DNA
<213> ORGANISM: Homo sapiens

<400> SEQUENCE: 26
agtattagta actactgggg c                                                 21

<210> SEQ ID NO 27
<211> LENGTH: 16
<212> TYPE: PRT
<213> ORGANISM: Homo sapiens

<400> SEQUENCE: 27

Ser Ile Tyr Tyr Ser Gly Ser Thr Asn Tyr Asn Pro Pro Leu Lys Ser
1               5                   10                  15

<210> SEQ ID NO 28
<211> LENGTH: 48
<212> TYPE: DNA
<213> ORGANISM: Homo sapiens

<400> SEQUENCE: 28
agtatctatt atagtgggag cacgaactac aatccgcccc tcaagagt                    48

<210> SEQ ID NO 29
<211> LENGTH: 7
<212> TYPE: PRT
<213> ORGANISM: Homo sapiens

<400> SEQUENCE: 29

Leu Thr Tyr Tyr Phe Asp Tyr
1               5

<210> SEQ ID NO 30
<211> LENGTH: 21
<212> TYPE: DNA
<213> ORGANISM: Homo sapiens

<400> SEQUENCE: 30
```

```
ctgacctact actttgatta c                                              21
```

<210> SEQ ID NO 31
<211> LENGTH: 11
<212> TYPE: PRT
<213> ORGANISM: Homo sapiens

<400> SEQUENCE: 31

Ser Gly Asp Lys Leu Gly Asp Lys Tyr Ala Cys
1               5                   10

<210> SEQ ID NO 32
<211> LENGTH: 33
<212> TYPE: DNA
<213> ORGANISM: Homo sapiens

<400> SEQUENCE: 32

```
tctggagata aattggggga taaatatgct tgc                                 33
```

<210> SEQ ID NO 33
<211> LENGTH: 7
<212> TYPE: PRT
<213> ORGANISM: Homo sapiens

<400> SEQUENCE: 33

Gln Asp Ser Lys Arg Pro Ser
1               5

<210> SEQ ID NO 34
<211> LENGTH: 21
<212> TYPE: DNA
<213> ORGANISM: Homo sapiens

<400> SEQUENCE: 34

```
caagatagca agcggccctc a                                              21
```

<210> SEQ ID NO 35
<211> LENGTH: 9
<212> TYPE: PRT
<213> ORGANISM: Homo sapiens

<400> SEQUENCE: 35

Gln Thr Trp Asp Ser Ser Thr Val Val
1               5

<210> SEQ ID NO 36
<211> LENGTH: 27
<212> TYPE: DNA
<213> ORGANISM: Homo sapiens

<400> SEQUENCE: 36

```
cagacgtggg acagcagcac tgtggta                                        27
```

<210> SEQ ID NO 37
<211> LENGTH: 5
<212> TYPE: PRT
<213> ORGANISM: Homo sapiens

<400> SEQUENCE: 37

Ser Tyr Ala Met Ser
1               5

<210> SEQ ID NO 38

```
<210> SEQ ID NO 38
<211> LENGTH: 15
<212> TYPE: DNA
<213> ORGANISM: Homo sapiens

<400> SEQUENCE: 38
agctatgcca tgagt                                                      15

<210> SEQ ID NO 39
<211> LENGTH: 17
<212> TYPE: PRT
<213> ORGANISM: Homo sapiens

<400> SEQUENCE: 39

Gly Phe Ser Gly Ser Gly Phe Ile Thr Tyr Tyr Ala Asp Ser Val Lys
1               5                   10                  15
Gly

<210> SEQ ID NO 40
<211> LENGTH: 51
<212> TYPE: DNA
<213> ORGANISM: Homo sapiens

<400> SEQUENCE: 40
ggttttagtg gtagtggttt tattacatac tacgcagact ccgtgaaggg c             51

<210> SEQ ID NO 41
<211> LENGTH: 12
<212> TYPE: PRT
<213> ORGANISM: Homo sapiens

<400> SEQUENCE: 41

Pro Pro Arg Gly Tyr Asn Tyr Gly Pro Phe Asp Tyr
1               5                   10

<210> SEQ ID NO 42
<211> LENGTH: 36
<212> TYPE: DNA
<213> ORGANISM: Artificial Sequence
<220> FEATURE:
<223> OTHER INFORMATION: Recombinant

<400> SEQUENCE: 42
cctcctcgtg gatacaacta tggcccttttt gactac                             36

<210> SEQ ID NO 43
<211> LENGTH: 117
<212> TYPE: PRT
<213> ORGANISM: Homo sapiens

<400> SEQUENCE: 43

Gln Leu Gln Leu Gln Glu Ser Gly Pro Gly Leu Val Lys Pro Ser Glu
1               5                   10                  15

Ser Leu Ser Leu Thr Cys Thr Val Ser Gly Gly Ser Ile Ser Ile Arg
                20                  25                  30

Thr Tyr Tyr Trp Gly Trp Ile Arg Gln Pro Pro Gly Thr Gly Leu Glu
            35                  40                  45

Trp Met Gly Tyr Ile Tyr Tyr Ser Gly Ser Thr Arg Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg Leu Ser Tyr Phe Phe Asp Tyr Trp Gly Gln Gly Thr Leu
            100                 105                 110

Val Thr Val Ser Ser
        115

<210> SEQ ID NO 44
<211> LENGTH: 351
<212> TYPE: DNA
<213> ORGANISM: Homo sapiens

<400> SEQUENCE: 44
cagctgcaac tgcaggagtc gggcccagga ctggtgaagc cttcggagtc cctgtccctc      60
acctgcactg tctctggtgg ctccatcagc attagaactt actactgggg ctggatccgc     120
cagcccccag ggacggggct ggagtggatg gggtatatct attatagtgg agcaccccgc     180
tacaacccgt ccctcaagag tcgagtcacc atatccgtag acacgtccaa gaaccagttc     240
tccctgaagc tgagctctgt gaccgccgca gacacggctg tgtattactg tgcgagactt     300
agctacttct ttgactactg gggccaggga accctggtca ccgtctccta a              351

<210> SEQ ID NO 45
<211> LENGTH: 106
<212> TYPE: PRT
<213> ORGANISM: Homo sapiens

<400> SEQUENCE: 45

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Met Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Leu Ala Met
65                  70                  75                  80

Asp Glu Ala Asp Tyr Tyr Cys Gln Ala Trp Asp Ser Gly Thr Val Ile
                85                  90                  95

Phe Gly Gly Gly Thr Lys Leu Thr Val Leu
            100                 105

<210> SEQ ID NO 46
<211> LENGTH: 318
<212> TYPE: DNA
<213> ORGANISM: Homo sapiens

<400> SEQUENCE: 46
tcctatgaac tgactcagcc accctcagtg tccgtgtccc caggacagac agccagcatc      60
acctgctctg gagataaaatt ggggataaaa tatgcttgct ggtatcagca gaagccaggc     120
cagtcccctg tgatggtcat ctatcaagat accaagcggc cctcagggat ccctgagcga     180
ttctctggct ccaactctgg gaacacagcc actctgacca tcagcgggac cctggctatg     240
gatgaggctg actattattg tcaggcgtgg gacagcggca ctgtgatatt cggcggaggg     300
accaagctga ccgtcccta                                                 318

<210> SEQ ID NO 47
<211> LENGTH: 121
```

<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Pro Arg Gly Tyr Asn Tyr Gly Pro Phe Asp Tyr Trp Gly
            100                 105                 110

Gln Gly Thr Leu Val Thr Val Ser Ser
        115                 120

<210> SEQ ID NO 48
<211> LENGTH: 363
<212> TYPE: DNA
<213> ORGANISM: Homo sapiens

<400> SEQUENCE: 48
gaggtgcaac tgttggagtc tgggggaggc ttggtacagc ctggggggtc cctgagactc      60
tcctgtgcag cctctggatt cacctttagc agctatgcca tgagttgggt ccgccaggct     120
ccagggaagg ggctggagtg ggtctcaggt attagtggta gtggtggttt cacttactac     180
gcagactccg tgaagggccg gttcaccatc tccagagaca attccaagaa cacgctgtat     240
ctgcaaatga acagcctgag agccgaggac acggccgtat attactgtgc gaaacctcct     300
cgtggataca actatggccc ttttgactac tggggccagg gaaccctggt caccgtctcc     360
tca                                                                  363

<210> SEQ ID NO 49
<211> LENGTH: 108
<212> TYPE: PRT
<213> ORGANISM: Homo sapiens

<400> SEQUENCE: 49

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 50
<211> LENGTH: 324
<212> TYPE: DNA
<213> ORGANISM: Homo sapiens

<400> SEQUENCE: 50

```
tcctatgtgc tgactcagcc accctcggtg tcagtggccc caggacagac ggccaggatt    60
acctgtgggg gaaacaacat tggaagtaaa agtgtacact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg atagtagta gtgatcacgt ggtattcggc   300
ggagggacca agctgaccgt ccta                                          324
```

<210> SEQ ID NO 51
<211> LENGTH: 117
<212> TYPE: PRT
<213> ORGANISM: Homo sapiens

<400> SEQUENCE: 51

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ile
             20                  25                  30

Ser Asn Tyr Trp Gly Trp Ile Arg Gln Pro Pro Gly Lys Gly Leu Glu
         35                  40                  45

Trp Ile Gly Ser Ile Tyr Tyr Ser Gly Ser Thr Asn Tyr Asn Pro Pro
     50                  55                  60

Leu Lys Ser Arg Val Thr Ile Ser Val Asp Thr Thr Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu Thr Tyr Tyr Phe Asp Tyr Trp Gly Gln Gly Met Leu
            100                 105                 110

Val Thr Val Ser Ser
        115
```

<210> SEQ ID NO 52
<211> LENGTH: 351
<212> TYPE: DNA
<213> ORGANISM: Homo sapiens

<400> SEQUENCE: 52

```
cagctgcagc tgcaggagtc gggcccagga ctggtgaagc cttcggagac cctgtccctc    60
acctgcactg tctctggtgg ctccatcagc agtattagta actactgggg ctggatccgc   120
cagcccccag gaagggggct ggagtggatt ggagtatct attatagtgg gagcacgaac   180
tacaatccgc ccctcaagag tcgagtcacc atatccgtag acacgaccaa gaaccagttc   240
tccctgaagc tgagctctgt gaccgccgca gacacggctg tgtattactg tgcgagactg   300
acctactact tgattactg gggccaggga atgctggtca ccgtctcctc a             351
```

<210> SEQ ID NO 53
<211> LENGTH: 106
<212> TYPE: PRT
<213> ORGANISM: Homo sapiens -continued

<400> SEQUENCE: 53

Ser Tyr Asp Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Leu Leu Val Ile Gln
        35                  40                  45

Gln Asp Ser Lys Arg Pro Ser Gly Ile Pro Ala Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Thr Trp Asp Ser Ser Thr Val Val
                85                  90                  95

Phe Gly Gly Gly Thr Lys Leu Thr Val Leu
            100                 105

<210> SEQ ID NO 54
<211> LENGTH: 318
<212> TYPE: DNA
<213> ORGANISM: Homo sapiens

<400> SEQUENCE: 54
tcctatgacc tgactcagcc accctcagtg tccgtctccc caggacagac agccagcatc    60
acctgctctg gagataaatt gggggataaa tatgcttgct ggtatcagca gaagccaggc   120
cagtcccctt tgctggtcat ccagcaagat agcaagcggc cctcagggat ccctgcgcga   180
ttctctggct ccaactctgg gaacacagcc actctgacca tcagcgggac ccaggctatg   240
gatgaggctg actatttctg tcagacgtgg gacagcagca ctgtggtatt cggcggaggg   300
accaagctga ccgtccta                                                  318

<210> SEQ ID NO 55
<211> LENGTH: 121
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Phe Ser Gly Ser Gly Phe Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Met Pro Pro Arg Gly Tyr Asn Tyr Gly Pro Phe Asp Tyr Trp Gly
            100                 105                 110

Gln Gly Thr Leu Val Thr Val Ser Ser
        115                 120

<210> SEQ ID NO 56
<211> LENGTH: 363
<212> TYPE: DNA

```
<213> ORGANISM: Homo sapiens

<400> SEQUENCE: 56
gaggtgcagt tgttggagtc tgggggaggc ttggtacagc ctggggggtc cctgagactc      60
tcctgtgcag cctctggatt caccttagc agctatgcca tgagttgggt ccgccaggct      120
ccagggaagg ggctggagtg ggtctcaggt tttagtggta gtggttttat tacatactac     180
gcagactccg tgaagggccg gttcaccatc tccagagaca attccaagaa tacgctgtat     240
ctgcaaatga acagcctgag agccgaggac acggccgtat attactgtgc gatgcctcct    300
cgtggataca actatggccc ttttgactac tggggccagg gaaccctggt caccgtctcc    360
tca                                                                   363
```